United States Patent [19]

Levitt

[11] 4,391,627

[45] Jul. 5, 1983

[54] HERBICIDAL BENZOTHIOPHENE AND BENZOFURAN SULFONAMIDES

[75] Inventor: George Levitt, Wilmington, Del.

[73] Assignee: E. I. Du Pont de Nemours and Company, Wilmington, Del.

[21] Appl. No.: 274,233

[22] Filed: Jun. 22, 1981

Related U.S. Application Data

[63] Continuation-in-part of Ser. No. 172,997, Jul. 25, 1980, abandoned.

[51] Int. Cl.[3] .................... A01N 43/54; C07D 239/26

[52] U.S. Cl. .......................................... 71/90; 71/92; 71/93; 544/212; 544/253; 544/278; 544/292; 544/321; 544/324; 544/331; 548/466; 549/54; 549/55; 549/56; 549/466

[58] Field of Search ............... 544/321, 324, 331, 212, 544/253, 278, 292; 71/90, 92, 93

[56] References Cited

U.S. PATENT DOCUMENTS

| | | | |
|---|---|---|---|
| 4,127,405 | 11/1978 | Levitt | 71/93 |
| 4,169,719 | 10/1979 | Levitt | 544/331 |
| 4,231,784 | 11/1980 | Levitt | 544/321 |

FOREIGN PATENT DOCUMENTS

| | | |
|---|---|---|
| 174510 | 5/1963 | Argentina . |
| 121788 | 4/1964 | Netherlands . |

OTHER PUBLICATIONS

A. A. Abou Ouf et al., J. Drug Res. Egypt, 1974, pp. 123–129, vol. 6, No. 2.

*Primary Examiner*—Donald G. Daus

*Assistant Examiner*—M. C. Eakin

[57] ABSTRACT

Novel N-(heterocyclicaminocarbonyl)carbonyl-substituted benzothiophene- and benzofuransulfonamides are useful as herbicides. The invention also includes novel sulfonamides and sulfonyl isocyanates useful in preparing such compounds.

35 Claims, No Drawings

HERBICIDAL BENZOTHIOPHENE AND BENZOFURAN SULFONAMIDES

RELATED APPLICATION

This application is a continuation-in-part of my copending application U.S. Ser. No. 172,997, filed July 25, 1980, now abandoned.

BACKGROUND OF THE INVENTION

This invention relates to N-(heterocyclicaminocarbonyl)carbonyl-substituted benzothiophene- and benzofuransulfonamides which are useful as herbicides. The invention also includes novel sulfonamides and sulfonyl isocyanates used in preparing such compounds.

Netherlands Patent No. 121,788, published Sept. 15, 1966, teaches the preparation of compounds of Formula (I), and their use as general or selective herbicides:

(I)

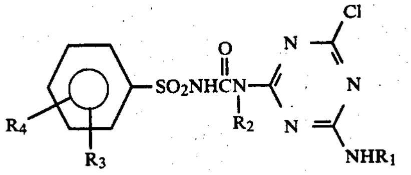

wherein $R_1$ and $R_2$ may independently be alkyl of 1–4 carbon atoms; and $R_3$ and $R_4$ may independently be hydrogen, chlorine or alkyl of 1–4 carbon atoms.

Compounds of Formula (II), and their use as antidiabetic agents, are reported in J. Drug. Res. 6, 123 (1974):

(II)

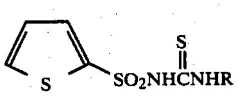

wherein R is pyridyl.

In U.S. Pat. No. 4,127,405, compounds are disclosed of the general formula:

(I)

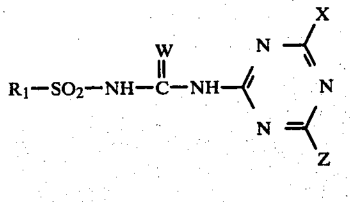

wherein $R_1$ is

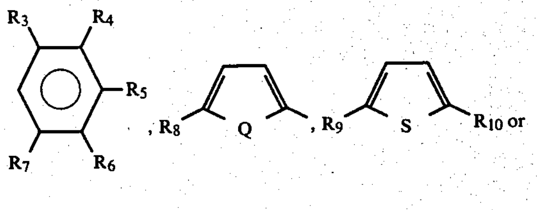

-continued

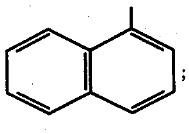

;

$R_3$ and $R_6$ are independently hydrogen, fluorine, chlorine, bromine, iodine, alkyl of 1-4 carbon atoms, alkoxy of 1-4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1-2 carbon atoms or alkoxy of 1-2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S$— or $CH_3OCH_2$—; and Z is methyl or methoxy; or their agriculturally suitable salts, provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

In particular, the patent discloses ortho-substituted compounds wherein the substitution is $C_1$–$C_4$ alkyl.

Argentine Patent No. 174,510 (issued Feb. 14, 1963 to Deutsche Gold und Silber) disclosed, among others, herbicidal compositions of sulfonylureas (i)

(i)

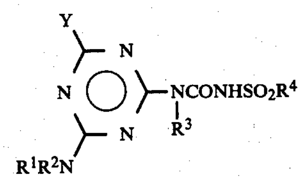

wherein $R^1$, $R^2$ and $R^3$ are independently H, alkyl or alkenyl;

$R^4$ is substituted aryl; and

Y is Cl, $CH_3$, $CH_2Cl$, $CHCl_2$ or $CCl_3$.

Specifically taught are herbicidal sulfonylureas where $R^4$ is p-chloro or p-methylphenyl;

$R^1$ and $R^3$ are $C_2H_5$ or i-$C_3H_7$;

$R^2$ is H; and

Y is Cl or $CH_3$.

The presence of undesired vegetation causes substantial damage to useful crops, especially agricultural products that satisfy man's basic food needs, such as soybeans, corn, wheat, and the like. The current population explosion and concomitant world food shortage demand improvements in the efficiency of producing these crops. Preventing or minimizing the loss of a portion of valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. However, the need exists for still more effective herbicides that destroy or retard weeds without causing significant damage to useful crops.

SUMMARY OF THE INVENTION

This invention relates to novel compounds of Formula I, suitable agricultural compositions containing them, and their method-of-use as general, as well as, selective pre-emergence and/or post-emergence herbicides and as plant growth regulants.

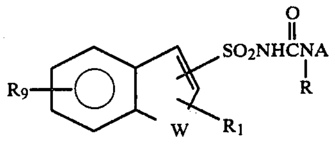

I wherein

R is H or $CH_3$;

$R^1$ is H, Cl, Br, $NO_2$, $C_1$–$C_3$ alkyl, $C_1$–$C_3$ alkoxy, $CO_2R^2$, $C(O)NR^3R^4$, $SO_2R$ or $SO_2NR^6R^7$;

$R^2$ is $C_1$–$C_4$ alkyl, $C_3$–$C_4$ alkenyl, $CH_2CH_2OCH_3$, $CH_2CH_2OC_2H_5$, $CH_2CH_2CH_2OCH_3$ or $CH_2R^8$;

$R^3$ is $C_1$–$C_4$ alkyl;

$R^4$ is H, $C_1$–$C_4$ alkyl or $OCH_3$; or $R^3$ and $R^4$ can be taken together to form $-(CH_2)_4-$;

$R^5$ is $C_1$–$C_4$ alkyl;

$R^6$ is $C_1$–$C_3$ alkyl or $OCH_3$;

$R^7$ is $C_1$–$C_3$ alkyl;

$R^8$ is $C_1$–$C_3$ alkyl substituted with 1–3 atoms of F, Cl, or Br;

$R^9$ is H, $CH_3$, $OCH_3$, Cl, Br or $NO_2$;

W is O or S;

A is

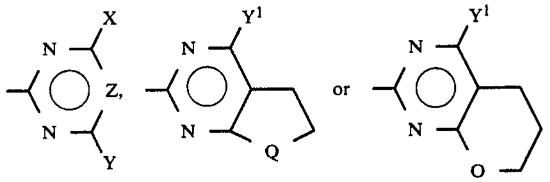

X is H, $CH_3$, $OCH_3$, $OC_2H_5$, $OCH_2CF_3$, $CH_2OCH_3$ or Cl;

Y is $CH_3$; $OCH_3$, $OC_2H_5$, $NH_2$, $NHCH_3$, $N(CH_3)_2$ or $SCH_3$;

Z is N, CH, C—Cl, C—Br, C—CN, C—$CH_3$, C—$C_2H_5$, C—$CH_2CH_2Cl$ or C—$CH_2CH{=}CH_2$;

$Y^1$ is H, $CH_3$, $OCH_3$ or Cl; and

Q is O or $CH_2$;

provided that (1) when $R^4$ or $R^6$ is $OCH_3$, then $R^3$ or $R^7$ is $CH_3$;

(2) the total number of carbon atoms of either $R^3$ and $R^4$, or $R^6$ and $R^7$, is less than or equal to 4; and (3) when X is Cl, then Z is CH.

Preferred for reasons of higher herbicidal activity and/or more favorable ease of synthesis are:

(1) Compounds of Formula I wherein Z is N or CH; and $R^1$ is H, Cl, Br, $NO_2$, $C_1$–$C_3$ alkyl, $CO_2R^2$, $SO_2R^5$ or $SO_2NR^6R^7$;

(2) Compounds of Preferred (1) wherein $R^9$ is H;

(3) Compounds of Preferred (2) wherein R is H;

(4) Compounds of Preferred (3) wherein A is

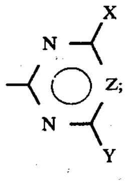

X is $CH_3$, $OCH_3$, $OC_2H_5$ or $CH_2OCH_3$; and Y is $CH_3$ or $OCH_3$;

(5) Compounds of Preferred (4) wherein W is S;

(6) Compounds of Preferred (5) wherein $R^1$ is Cl, Br, $NO_2$, $CO_2R^2$, $SO_2R^5$ or $SO_2NR^6R^7$;

(7) Compounds of Preferred (6) wherein $R^1$ is at the 2-position of the benzo[b]thiophene ring; and (8) Compounds of Preferred (7) wherein $R^1$ is $CO_2R^2$.

Specifically preferred are:

3-[[(4,6-dimethylpyrimidin-2-yl)aminocarbonyl]aminosulfonyl]benzo[b]thiophene-2-carboxylic acid, methyl ester, m.p. 207°–208°;

3-[[(4,6-dimethoxypyrimidin-2-yl)aminocarbonyl]aminosulfonyl]benzo[b]thiophene-2-carboxylic acid, methyl ester, m.p. 209°–210°;

3-[[(4-methoxy-6-methylpyrimidin-2-yl)aminocarbonyl]aminosulfonyl]benzo[b]thiophene-2-carboxylic acid, methyl ester, m.p. 108°–111° (dec);

3-[[(4,6-dimethyl-1,3,5-triazin-2-yl)aminocarbonyl]aminosulfonyl]benzo[b]thiophene-2-carboxylic acid, methyl ester, m.p. 195°–198°;

3-[[(4,6-dimethoxy-1,3,5-triazin-2-yl)aminocarbonyl]aminosulfonyl]benzo[b]thiophene-2-carboxylic acid, methyl ester, m.p. 193°–195°;

3-[[(4-methyl-6-methoxy-1,3,5-triazin-2-yl)aminocarbonyl]aminosulfonyl]benzo[b]thiophene-2-carboxylic acid, methyl ester, m.p. 185°–195°; and 3-[[(4,6-dimethoxypyrimidin-2-yl)aminocarbonyl]aminosulfonyl]benzo[b]thiophene-2-carboxylic acid, ethyl ester.

This invention also relates to the following novel compounds which are useful intermediates for the preparation of the herbicides of Formula I:

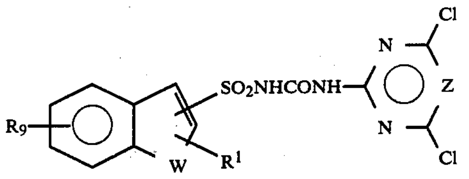

(A)

wherein $R^1$, $R^9$ and W are as previously defined; and

Z is N or CH.

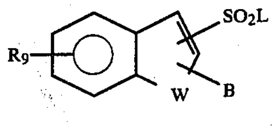

(B)

wherein

L is NCO;

B is $CO_2R^2$, $SO_2R^5$, $SO_2NR^6R^7$, Cl, Br, H, $NO_2$, $C_1$-$C_3$ alkyl or $C_1$-$C_3$ alkoxy; and $R^2$, $R^5$, $R^6$, $R^7$, $R^9$ and W are as previously defined;

provided that (1) when $R^6$ is $OCH_3$, then $R^7$ is $CH_3$; and (2) the total number of carbon atoms of $R^6$ and $R^7$ is less than or equal to 4.

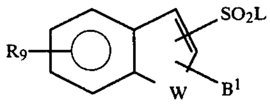

(C)

wherein

L is Cl or $NH_2$;

$B^1$ is $CO_2R^2$, $SO_2R^5$, $SO_2NR^6R^7$, $C(O)NR^3R^4$, Cl, Br, $NO_2$ or $C_2$-$C_3$ alkyl or $C_1$-$C_3$ alkoxy; and $R^2$, $R^3$, $R^4$, $R^5$, $R^6$, $R^7$, $R^9$ and W are as previously defined;

provided that (1) when $R^4$ or $R^6$ is $OCH_3$, then $R^3$ or $R^7$ is $CH_3$; and (2) the toal number of carbon atoms of either $R^3$ and $R^4$, or $R^6$ and $R^7$, is less than or equal to 4.

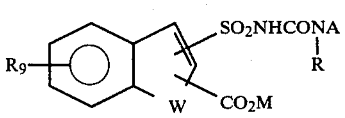

(D)

wherein

M is H or alkali metal ion; and

R, $R^9$, W and A are as previously defined;

provided that X and $Y^1$ are other than Cl.

Synthesis

As shown in Equation 1, the compounds of Formula I can be prepared by combining an appropriate 2-aminoheterocycle of Formula III with an appropriately substituted sulfonyl isocyanate of Formula II; B, R, W and A being as previously defined.

Equation 1

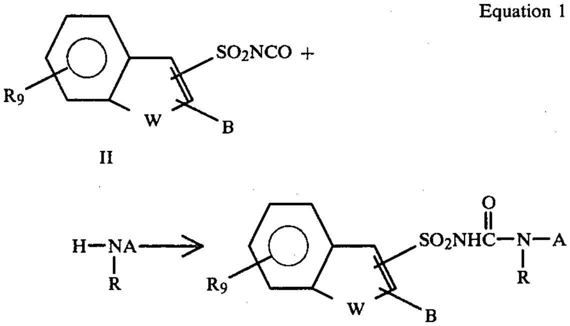

II

III I

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of the aminoheterocycle. Since isocyanates usually are liquids, their addition can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane, ethyl ether, or pentane and filtration.

The intermediate sulfonyl isocyanates of Formula II can be prepared by reacting corresponding sulfonamides with phosgene in the presence of an alkyl isocyanate such as butyl or cyclohexyl isocyanate at reflux in a solvent such as chlorobenzene, according to the procedure of H. Ulrich and A. A. Y. Sayigh, *Newer Methods of Preparative Organic Chemistry,* Vol. VI, p. 223-241, Academic Press, New York and London, W. Forest Ed. In cases where formation of the desired sulfonyl isocyanate is difficult by the above procedure, the preformed sulfonylurea from the reaction of butyl isocyanate with the appropriate sulfonamide is treated with phosgene according to the above reference.

Alternatively, the process of Ulrich and Sayigh can be improved by the addition of a tertiary base to the reaction mixture as shown by Equation 2.

Equation 2

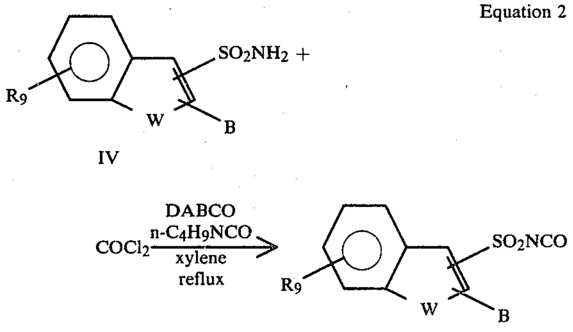

IV

II

A mixture of the appropriate benzenesulfonamide IV, an alkyl isocyanate such as butyl isocyanate and a catalytic amount of 1,4-diaza[2,2,2]bicyclooctane (DABCO) in xylene or other inert solvent of sufficiently high boiling point (e.g. 135° C.) is heated to approximately 135° C. Phosgene is added to the mixture until an excess is present as indicated by a drop in the boiling point. (The mixture is heated further to drive off the excess phosgene). After the mixture is cooled and filtered to remove a small amount of insoluble by-products, the solvent and alkyl isocyanate are distilled off in vacuo leaving a residue which is the crude sulfonyl isocyanate II.

The preparation of sulfonamides from ammonium hydroxide or anhydrous ammonia and sulfonyl chlorides is widely reported in the literature, e.g., Crossley et al., *J. Am. Chem. Soc.,* 60, 2223 (1938). The sulfonyl chloride intermediates used for the preparation of the sulfonamides of structure IV can be prepared as outlined in Equation 3. Benzothiophene and benzofuran sulfonic acids are known in the literature. E. Guenther et al., *Z. Chem.,* 81, 111 (1968) *Chem. Abs.,* 68, 104665 (1968) report the preparation of 2-benzofuransulfonyl chloride from benzofuran and $S_2O_5Cl_2$. 3-Benzothiophenesulfonic acid is prepared by the sulfonation of benzothiophene according to M. Pailer and E. Romberger, *Monatsch,* 92, 677 (1961). As shown in Equation 3 we have found that amino substituted benzothiophenes and benzofurans (Structure V) treated with nitrous acid form diazonium salts (Structure VI) which react with sulfur dioxide in hydrochloric acid in the presence of cupric chloride to form the desired sulfonyl chloride (Structure VII). $B^1$ and W being as previously defined.

Equation 3

(a).

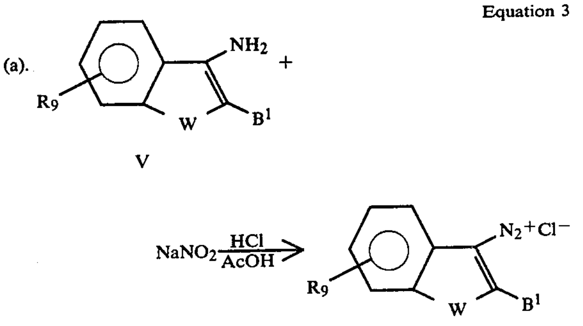

V

VI (b).

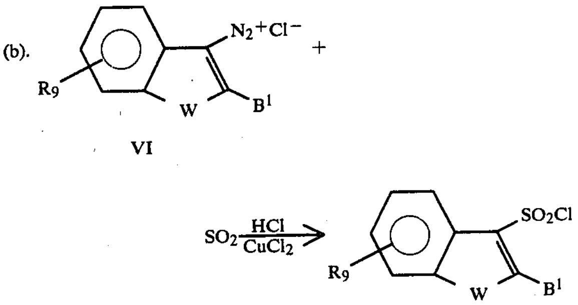

VI

VII

The reactions of Equation 3 are best carried out by adding the amine to an acetic acid, hydrochloric acid mixture at −10° to 0° C. followed by the dropwise addition of an aqueous solution of sodium nitrite at 0° C. Alternatively propionic acid can be used in place of acetic acid or the amount of hydrochloric acid is increased and no acetic acid is used. After stirring for ½ to 1 hour this solution is added to acetic acid or hydrochloric acid containing 2 to 10 molar equivalents of sulfur dioxide and a catalytic quantity of cuprous or cupric ion, preferably, a chloride salt. The resultant mixture is stirred at 0° to 25° C. for a period of one to twenty-four hours. It is then poured into an equal volume of ice water. In some cases the desired sulfonyl chloride precipitates as a solid or it can be extracted into methylene chloride and isolated from the solvent.

Electrophilic substitution reactions such as sulfonation with $S_2O_5Cl_2$ as mentioned above occur almost exclusively in the 2-position in benzofuran while benzothiophene is substituted predominantly in the 3-position. When these positions are substituted previously by a group such as halogen, alkyl or alkoxy the sulfonation reactions take place at the unsubstituted 2 or 3 position. Benzothiophene undergoes lithiation with butyl lithium or a lithium dialkylamide such as lithium diisopropylamide (LDA) to yield a 2-lithiobenzothiophene (Structure IX) as shown in *Tetrahedron,* 29, 321 (1973) or as more generally described in *Organic Reactions,* Vol. 26, Chapter 1, John Wiley and Sons, Inc., New York, 1979, W. G. Dauben, Ed. in Chief. As shown in Equation 4 sulfur dioxide can react with the lithio salt to yield the 2-sulfinic acid (Structure X) which can be chlorinated to the sulfonylchloride (Structure XI).

Equation 4

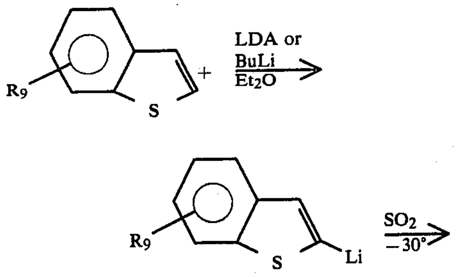

IX (b).

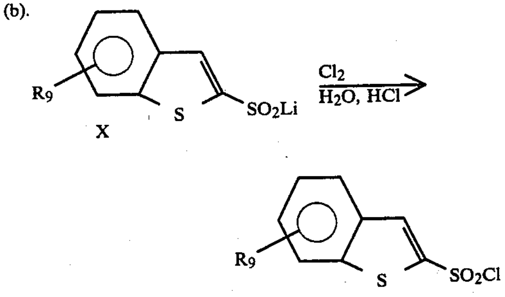

X

XI

Treatment of this sulfonyl chloride with $NH_3$ source yields the sulfonamide which can be converted to the sulfonyl isocyanate as shown in Equation 2. When XI is reacted with $HNR_6R_7$ where $R_6$ and $R_7$ are as previously defined the product obtained is the sulfonamide (XII) as shown in Equation 5. Lithiation of this compound yields the 3-lithio salt (XIII) which reacts with sulfur dioxide to yield the 3-sulfinic acid lithio salt XIV. This derivative can be converted to the sulfonyl chloride by chlorination in water-hydrochloric acid as described for Equation 4 and treated with ammonium hydroxide or anhydrous ammonia to yield a 2-(N,N-dialkylsulfamoyl)benzothiophen-3-sulfonamide which can be converted to the sulfonyl isocyanate as described in Equation 2. When the sequence of reactions described in Equation 5 is applied to a benzothiophene-3-sulfonyl chloride rather than Structure XI, a 3-(N,N-dialkylsulfamoyl)benzothiophene-2-sulfonamide is obtained. The same sequence of reactions as shown in Equations 4 and 5 can be followed for the preparation of the analogous benzofuran derivatives of this invention.

Equation 5

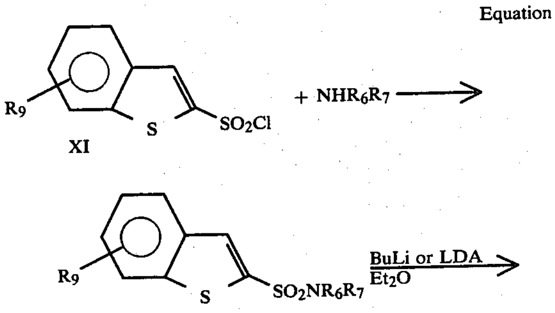

XI

XII

XII

-continued

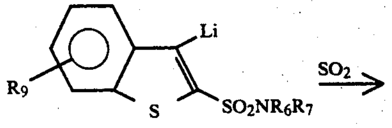

XIII

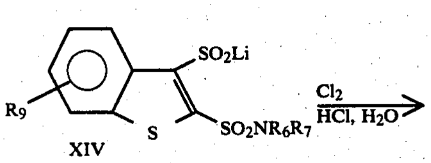

XIV

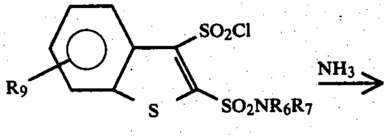

XV

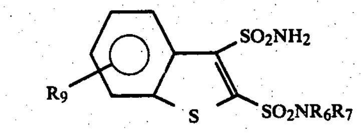

XVI

Sulfonamide intermediates for the preparation of the herbicidal compounds of this invention where $R_1$ is $CO_2R^2$, $CONR^3R^4$ are prepared according to Equation 6 where W is O or S.

Equation 6

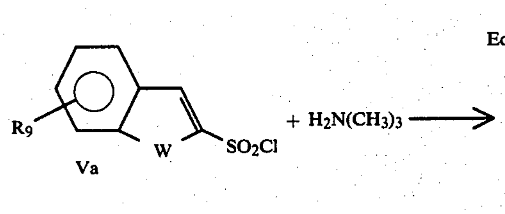

Va

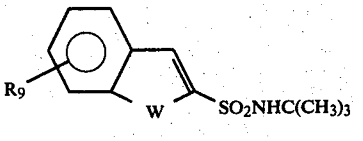

XVII

Lithiation of XVII with 2 moles of butyl lithium or LDA yields the 3 lithio salt which on treatment with carbon dioxide forms the 3-carboxy lithio salt as shown in Equation 7.

Equation 7

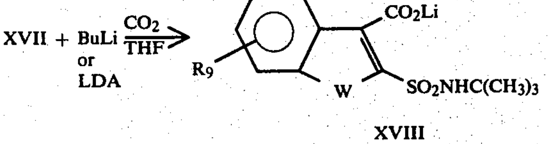

XVIII

-continued

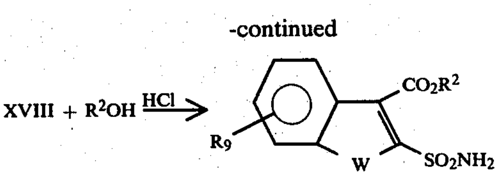

XIX

The lithium salt, XVIII, is converted to the parent acid and the acid is treated with an alcohol of the formula $R^2OH$, in the presence of an acid catalyst such as toluenesulfonic acid, a mineral acid like sulfuric acid or hydrochloric acid or a strong acid ion exchange resin to yield the ester XIX. The esterification is best carried out at 30°-100° C. in the presence of an excess of the alcohol being used. Upon completion of the reaction the product is isolated by removal of the excess alcohol in vacuo dissolving the product in a neutral organic solvent such as methylene chloride, extracting the salts present with water and isolating the ester by evaporation of the solvent.

The synthesis of heterocyclic amine derivatives has been reviewed in "The Chemistry of Heterocyclic Compounds", a series published by Interscience Publ., New York and London. 2-Aminopyrimidines are described by D. J. Brown in "The Pyrimidines", Vol. XVI of the above series. The 2-amino-1,3,5-triazines are reviewed by E. M. Smolin and L. Rapaport in "s-Triazines and Derivatives," Vol. XIII of the same series. The synthesis of triazines is also described by F. C. Schaefer, U.S. Pat. No. 3,154,547 and by K. R. Huffman and F. C. Schaefer, *J. Org. Chem.*, 28, 1812-1821 (1963).

The preparation of fused ring pyrimidine amines is disclosed in various publications, such as: Braken et al., *J. Am. Chem. Soc.*, 69, 3072 (1947); Mitten and Bharlacharya, *Quart. J. Ind. Chem. Soc.*, 4, 152 (1927), Schrage and Hitchings, *J. Org. Chem.*, 16, 1153 (1951); Svab et al., Coll. Czech Commun. 32, 1582 (1967).

Compounds of Formula I can also be prepared by the method described in Equation 8.

Equation 8

(8a).

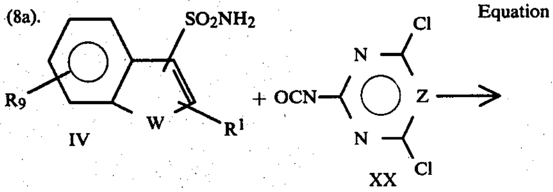

IV XX

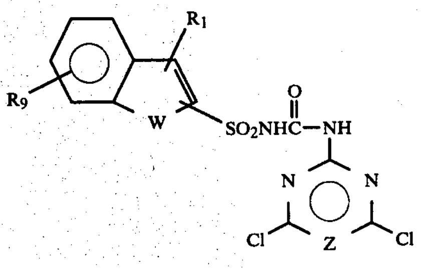

XXI

-continued (8b).
XXI

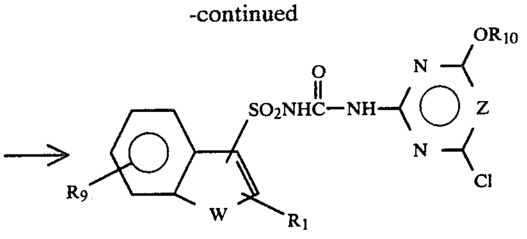

XXII (8c).
XXII

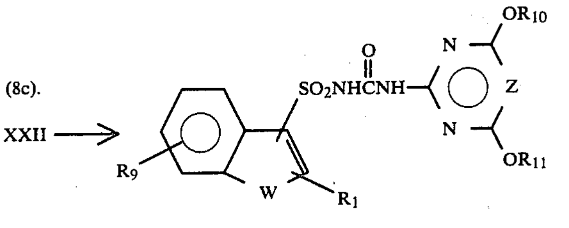

XXIV wherein
$R^1$ and W are as defined previously;
$R_{10}$ is methyl, ethyl or $CH_2CF_3$;
$R_{11}$ is methyl or ethyl; and
Z is CH or N.

Reaction Step (8a)

In Reaction step (8a), a sulfonamide of Formula IV is contacted with a heterocyclic isocyanate of Formula XX to yield an N-(haloheterocyclicaminocarbonyl-)aromatic sulfonamide of Formula XXI.

The heterocyclic isocyanates used in Reaction (8a) may be prepared according to methods described in Swiss Patent No. 3,919,228, U.S. Pat. No. 3,732,223 and *Angew Chem. Int. Ed.,* 10, 402 (1976), the disclosures of which are herein incorporated by reference.

The aromatic sulfonamide and the heterocyclic isocyanate are contacted in the presence of an inert organic solvent, for example, acetonitrile, tetrahydrofuran (THF), toluene, acetone or butanone. Optionally, a catalytic amount of a base, such as 1,4-diazabicyclo[2.2.2]octane (DABCO), potassium carbonate, sodium hydride or potassium tert-butoxide, may be added to the reaction mixture. The quantity of base constituting a catalytic amount would be obvious to one skilled in the art. The reaction mixture is preferably maintained at a temperature of about 35° to 110° C., and the product can generally be recovered by cooling and filtering the reaction mixtuure. For reasons of efficiency and economy, the preferred solvents are acetonitrile and THF, and the preferred temperature range is about 60° to 85° C.

Reaction Steps (8b) and (8c)

In Reaction Steps (8b) and (8c), one or two of the halogen atoms on the heterocyclic ring of the compound of Formula XXII is displaced by a nucleophilic species. Generally this may be done by contacting the compound of Formula XXI either with alkanol, $R_{10}OH$ or with alkoxide, $—OR_{10}$, where $R_{10}$ is as defined above.

Thus, in Reaction Step (8b), a compound of Formula XXI can be contacted with at least one equivalent of alkanol, $R_{10}OH$. This reaction is sluggish, however, and it is preferred to contact the compound of Formula XXI with at least two equivalents of alkoxide, $—OR_{10}$. The alkoxide can be provided in a number of ways:

(a) The compound of Formula XXI can be suspended or dissolved in an alkanol solvent, $R_{10}OH$, in the presence of two equivalents of alkoxide, $OR_{10}$. The alkoxide can be added directly as alkali metal or alkaline earth metal alkoxide or can be generated by the addition to the alkanol solvent of at least two equivalents of a base capable of generating alkoxide from the solvent. Suitable bases include, but are not limited to, the alkali and alkaline earth metals, their hydrides and tert-butoxides. For example, when $R_{10}$ is methyl, the compound of Formula XXI could be suspended or dissolved in methanol in the presence of two equivalents of sodium methoxide. Alternatively, two equivalents of sodium hydride could be used in place of the sodium methoxide.

(b) The compound of Formula XXI can be suspended or dissolved in an inert solvent in the presence of at least two equivalents of alkoxide, $—OR_{10}$. Suitable inert solvents include, but are not limited to, acetonitrile, THF and dimethylformamide. The alkoxide may be added directly as alkali metal or alkaline earth metal alkoxide or may be generated from alkanol and a base as described in (a) above. For example, when $R_{10}$ is methyl, the compound of Formula XXI could be suspended or dissolved in THF in the presence of two equivalents of sodium methoxide. Alternatively, two equivalents each of methanol and sodium hydride could be used instead of sodium methoxide.

It should be noted that two equivalents of alkoxide are required for Reaction Step (8b) whereas only one equivalent of alkanol is needed for the same process. This difference is due to the reaction which is believed to occur between the alkoxide and the sulfonyl nitrogen of the sulfonamide of Formula XXI. When alkoxide is used, the first equivalent of alkoxide removes a proton from the sulfonyl nitrogen, and is only the second equivalent which effects displacement of the halogen. As a result, two equivalents of alkoxide are required. The resulting salt must be acidified, e.g., with sulfuric, hydrochloric or acetic acid, to yield a compound of Formula XXII. Applicant, of course, does not intend to be bound by the mechanism described above.

In Reaction Step (8c), a compound of Formula XXII, substituted with one chlorine atom is contacted with either one equivalent of alkanol, $R_{11}OH$, or with two equivalents of alkoxide, $—OR_{11}$ where $R_{11}$ is as described above. When alkoxide, $—OR_{11}$, is used, it may be provided in either of the methods described above in connection with Reaction Step (8b), and the resulting salt can be acidified to yield a compound of Formula XXIV.

When $R_{10}=R_{11}$, Reaction Steps (8b) and (8c) may be combined. Thus, a compound of Formula XXI may be contacted either with at least two equivalents of alkanol, $R_{11}OH$, or with at least three equivalents of alkoxide, $—OR_{11}$.

For a compound of Formula XXI, certain reaction conditions will favor displacement of only one chlorine atom. These conditions are the use of low temperatures and, when alkoxide is used, the slow addition of the stoichiometric amount of alkoxide or alkoxide-generating base to the medium containing the compound of Formula XXI.

When alkoxide is used, both Reaction Steps (8b) and (8c) are preferably run at temperatures within the range of about −10° C. to 80° C., the range of about 0° to 25° C. being more preferred. Reaction Steps (8b) and (8c) are more sluggish when alkanol is used instead of alkoxide, and more drastic conditions are required for the reaction to go to completion. Thus, higher temperatures, up to and including the boiling point of the alkanol itself, are required.

Compounds of Formula I can also be prepared by the method described in Equation 9, where an appropriately substituted benzothiophene or benzofuran of Formula XXV is contacted with an aminocarbonyl sulfamoyl chloride of Formula XXVI optionally in the presence of a Friedel-Crafts catalyst; R, $R^1$, $R_9$, W and A being as previously defined.

Equation 9

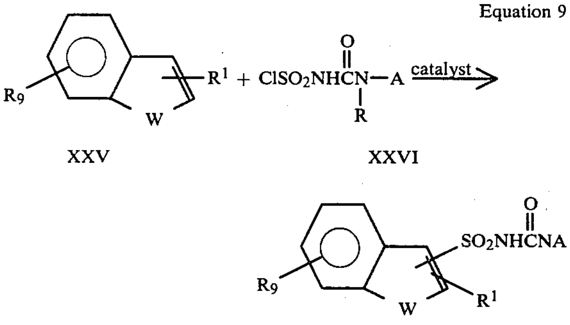

XXV XXVI

I

The reaction is best carried out in an inert solvent, including but not limited to, dichloromethane, nitroethane, nitropropanes, tetrahydrofuran or nitromethane in an inert atmosphere for 0.5 to 24 hours at temperatures ranging from 0° to the boiling point of the solvent employed. The preferred Friedel-Crafts catalyst is aluminum chloride, however, alternate catalysts may be used. Friedel-Crafts catalysts are extensively defined in Volume I, Chapter IV of "Friedel-Crafts and Related Reactions," ed. G. A. Olah, Interscience Publ., New York, 1963.

The compounds of Formula I may be isolated by partitioning the reaction mixture between dilute aqueous alkali and an organic solvent such as dichloromethane or chloroform. The products are soluble in the aqueous phase and may be precipitated by the addition of a slight excess of an acid such as acetic acid or hydrochloric acid. Products soluble in the acidified reaction medium are isolated by extraction into an organic solvent such as dichloromethane, nitromethane or ethyl acetate followed by evaporation of the solvent.

The intermediate aminocarbonyl sulfamoyl chlorides of Formula XXVI are prepared by contacting an appropriate 2-aminoheterocycle of Formula III with chlorosulfonyl isocyanate in an inert solvent such as tetrahydrofuran, dichloromethane or nitromethane at −80° to 0° C. for 0.1 to 1.0 hour under an inert atmosphere.

Equation 10

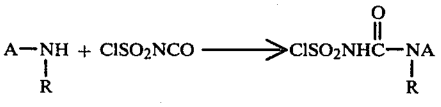

III XXVI where A is as previously defined.

The reaction is exothermic and is best carried out by addition of the chlorosulfonylisocyanate to a suspension of the heterocycle in the solvent of choice for the subsequent reaction of the product XXVI with compounds of Formula XXV. The products of Formula XXVI are highly reactive and are used without isolation in the synthesis of compounds of Formula I.

Compounds of Formula Ie can be prepared by hydrolysis of esters of Formula Id, wherein $R^2$ is $C_1$–$C_4$ alkyl and X, Y or Y' of A are not Cl. As shown in Equation 9, alkali metal base catalyzed hydrolysis in aqueous methanol produces the alkali metal carboxylate from which the carboxylic acid is obtained by treatment with mineral acids such as HCl:

Equation 11

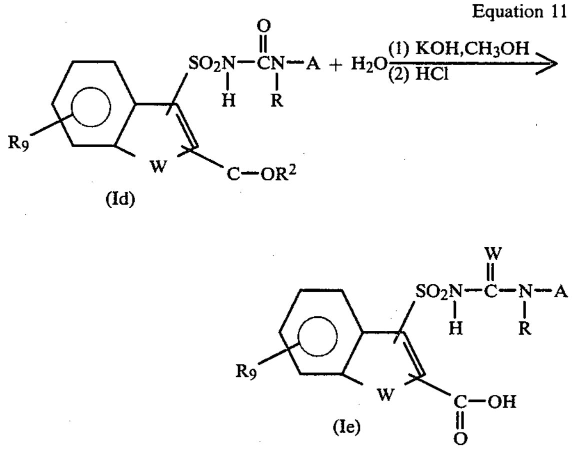

(Id)

(Ie)

The reaction of Equation 11 is best carried out in a solution cntaining the compound being hydrolyzed, 2 to 10 parts of methanol, 10–50 parts of water and 2–10 equivalents of a base such as sodium or potassium hydroxide maintaining the temperature at 30°–90° C. for 3–24 hours. The reaction yields the soluble alkali metal salt of the carboxylic acid, which is suitable for the purposes of this invention. Conversion of these salts to the acid form is easily carried out by addition to the reaction medium of strong mineral acids, such as hydrochloric or sulfuric acid, causing the desired carboxylic acids to precipitate from solution.

Compounds where $R_1$ is $CONR^3R^4$ can be prepared from esters of this invention where $R^2$ is $C_1$–$C_4$ (preferably $C_1$) by the reaction of the esters with dialkylaluminum-N-alkylamide derivatives according to Equation 12. R, A and W being as previously defined.

Equation 12

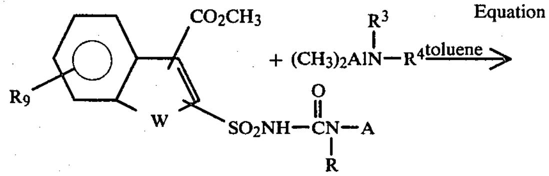

-continued

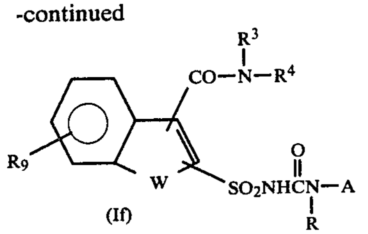

(If)

The intermediate alkylaminoaluminum compounds prepared according to A. Basha, M. Lipton and S. W. Weinreb, *Tetrahedron Letters* 4171 (1971), are comingled with a suspension of the esters in toluene, methylene chloride, or similar inert solvent and the mixture is refluxed for one to six hours. The product can be isolated by evaporation of the solvent adding methylene chloride and aqueous hydrochloric acid to decompose the residual reaction mass and extracting the desired product into methylene chloride. Evaporation of the methylene chloride yields the desired product in sufficiently pure form for the purpose of this invention.

Compounds of Formula Ie, prepared as shown in Equation 11, can be converted to compounds of this invention where $R^2$ is a higher alkyl or substituted hydrocarbyl group, as already disclosed herein, by the reaction of salts of the parent acid (M=H), with $R^2$-Halogen as shown in Equation 13.

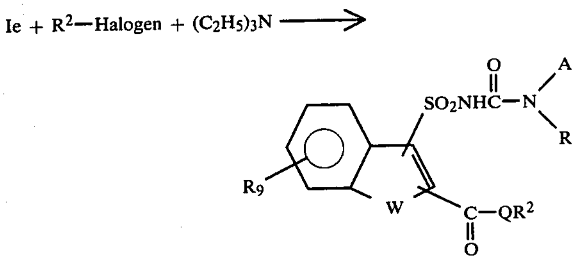

The reaction of Equation 13 is of particular use where the intermediate compound, R-Halogen, contains a readily replaceable halogen as is the case for allyl halides.

The procedure of Equation 13 is best carried out in inert polar solvents such as tetrahydrofuran, acetonitrile or acetone by combining the appropriately substituted carboxylic acid and base such as triethylamine or 1,4-diaza[2,2,2]bicyclooctane adding the appropriate halide and heating the mixture to reflux with stirring for 1 to 16 hours. The reaction mixture can be evaporated to dryness and the residue triturated with water, filtered and washed with water to separate the desired product from the water-soluble salt.

In the following examples all parts are by weight and all temperatures in °C. unless otherwise indicated.

EXAMPLE 1

Benzothiophene-3-sulfonyl isocyanate

Ten grams of benzothiophene-3-sulfonamide, 100 ml of xylene, 3 g. of butyl isocyanate and 0.1-0.3 g. of 1,4-diazabicyclo[2,2,2]octane in admixture were heated to reflux for one half hour after which phosgene was passed into the mixture for two hours at 125°. The reaction mixture was cooled, filtered and concentrated in vacuo to yield an oil (12 g.). Infrared analysis of this oil showed an absorption peak at 2250 $cm^{-1}$ consistent for the desired isocyanate.

EXAMPLE 2

Methyl 3-Isocyanatosulfonylbenzothiophene-2-carboxylate

Methyl 3-aminosulfonylbenzothiophene-2-carboxylate (10 grams), 75 ml of xylene, 3.5 g. of 3-butyl isocyanate and 0.2 g. of 1,4-diazabicyclo[2,2,2]octane in admixture were heated to reflux under a dry ice cooled reflux condenser for 10 minutes. Phosgene gas was passed into the system until the reflux temperature dropped to 120°. The addition was discontinued until the temperature rose to 130° and then additional phosgene was added to cause the temperature to drop to 120°. The cycle was repeated until the reflux temperature remained at 120° for one half hour with no further addition of phosgene. The mixture was then cooled, filtered and the filtrate was concentrated to remove the xylene and recovered butyl isocyanate. The residue thus obtained showed absorption peaks by infrared at 2200 and 1700 $cm^{-1}$ consistent for the isocyanate and carboxylate groups. This product was used for the synthesis of the herbicides of this invention without further purification. The isocyanate derivatives of Tables I-Ic can be prepared from the appropriately substituted sulfonamides by the method set forth in Examples 1 and 2.

TABLE I

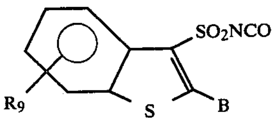

| B | $R_9$ |
|---|---|
| H | H |
| H | 4-Cl |
| $NO_2$ | H |
| $-CH_3$ | H |
| $-C_2H_5$ | 5-Br |
| Cl | H |
| Br | H |
| $-CH(CH_3)_2$ | H |
| $CH_3O-$ | 6-$OCH_3$ |
| $C_2H_5O-$ | H |
| $CH_3CH_2CH_2O-$ | H |
| $-CO_2CH_3$ | H |
| $-CO_2CH_3$ | 4-Cl |
| $-CO_2CH_3$ | 6-Cl |
| $-CO_2CH_3$ | 4-$NO_2$ |
| $-CO_2CH_3$ | 5-$NO_2$ |
| $-CO_2CH_3$ | 4-$OCH_3$ |
| $-CO_2CH_3$ | 5-$OCH_3$ |
| $-CO_2C_2H_5$ | H |
| $-CO_2CH(CH_3)_2$ | H |
| $-CO_2CH(CH_3)C_2H_5$ | H |
| $-CO_2CHCH=CH_2$ | 7-$CH_3$ |
| $-CO_2CH(CH_3)CH=CH_2$ | H |
| $-CO_2CHCHCH_3$ | H |
| $-CO_2CH_2CH_2Cl$ | 6-Br |
| $-CO_2CH_2CF_3$ | H |
| $-CO_2CH_2CH_2Br$ | H |
| $-CO_2CH_2CCl_3$ | H |
| $-CO_2CH_2CHCl_2$ | 4-$CH_3$ |
| $-CO_2CH_2CH_2OCH_3$ | H |
| $-CO_2CH_2CH_2OCH_2CH_3$ | H |
| $-CO_2CH_2CH_2CH_2OCH_3$ | H |
| $-SO_2CH_3$ | 7-Br |
| $-SO_2C_2H_5$ | H |
| $-SO_2CH(CH_3)_2$ | H |
| $-SO_2(CH_2)_3H$ | H |
| $-SO_2(CH_2)_4H$ | 5-$NO_2$ |
| $-SO_2N(CH_3)_2$ | H |

TABLE I-continued

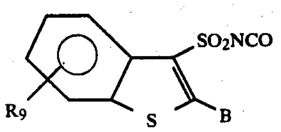

| B | $R_9$ |
|---|---|
| $-SO_2N(C_2H_5)_2$ | H |
| $SO_2NCH(CH_3)_2$<br>$\mid$<br>$CH_3$ | H |
| $-SO_2N(CH_3)OCH_3$ | 7-$OCH_3$ |

TABLE Ia

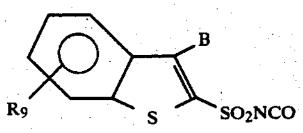

| B | $R_9$ |
|---|---|
| H | H |
| H | 4-Cl |
| $NO_2$ | H |
| $-CH_3$ | H |
| $-C_2H_5$ | 5-Br |
| Cl | H |
| Br | H |
| $-CH(CH_3)_2$ | H |
| $CH_3O-$ | 6-$OCH_3$ |
| $C_2H_5O-$ | H |
| $CH_3CH_2CH_2O-$ | H |
| $-CO_2CH_3$ | H |
| $-CO_2CH_3$ | 4-Cl |
| $-CO_2CH_3$ | 6-Cl |
| $-CO_2CH_3$ | 4-$NO_2$ |
| $-CO_2CH_3$ | 5-$NO_2$ |
| $-CO_2CH_3$ | 4-$OCH_3$ |
| $-CO_2CH_3$ | 5-$OCH_3$ |
| $-CO_2C_2H_5$ | H |
| $-CO_2CH(CH_3)_2$ | H |
| $-CO_2CH(CH_3)C_2H_5$ | H |
| $-CO_2CHCH=CH_2$ | 7-$CH_3$ |
| $-CO_2CH(CH_3)CH=CH_2$ | H |
| $-CO_2CHCHCH_3$ | H |
| $-CO_2CH_2CH_2Cl$ | 6-Br |
| $-CO_2CH_2CF_3$ | H |
| $-CO_2CH_2CH_2Br$ | H |
| $-CO_2CH_2CCl_3$ | H |
| $-CO_2CH_2CHCl_2$ | 4-$CH_3$ |
| $-CO_2CH_2CH_2OCH_3$ | H |
| $-CO_2CH_2CH_2OCH_2CH_3$ | H |
| $-CO_2CH_2CH_2CH_2OCH_3$ | H |
| $-SO_2CH_3$ | 7-Br |
| $-SO_2C_2H_5$ | H |
| $-SO_2CH(CH_3)_2$ | H |
| $-SO_2(CH_2)_3H$ | H |
| $-SO_2(CH_2)_4H$ | 5-$NO_2$ |
| $-SO_2N(CH_3)_2$ | H |
| $-SO_2N(C_2H_5)_2$ | H |
| $SO_2NCH(CH_3)_2$<br>$\mid$<br>$CH_3$ | H |
| $-SO_2N(CH_3)OCH_3$ | 7-$OCH_3$ |

TABLE Ib

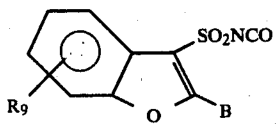

| B | $R_9$ |
|---|---|
| H | H |
| H | 4-Cl |
| $NO_2$ | H |
| $-CH_3$ | H |
| $-C_2H_5$ | 5-Br |
| Cl | H |
| Br | H |
| $-CH(CH_3)_2$ | H |
| $CH_3O-$ | 6-$OCH_3$ |
| $C_2H_5O-$ | H |
| $CH_3CH_2CH_2O-$ | H |
| $-CO_2CH_3$ | H |
| $-CO_2CH_3$ | 4-Cl |
| $-CO_2CH_3$ | 6-Cl |
| $-CO_2CH_3$ | 4-$NO_2$ |
| $-CO_2CH_3$ | 5-$NO_2$ |
| $-CO_2CH_3$ | 4-$OCH_3$ |
| $-CO_2CH_3$ | 5-$OCH_3$ |
| $-CO_2C_2H_5$ | H |
| $-CO_2CH(CH_3)_2$ | H |
| $-CO_2CH(CH_3)C_2H_5$ | H |
| $-CO_2CHCH=CH_2$ | 7-$CH_3$ |
| $-CO_2CH(CH_3)CH=CH_2$ | H |
| $-CO_2CHCHCH_3$ | H |
| $-CO_2CH_2CH_2Cl$ | 6-Br |
| $-CO_2CH_2CF_3$ | H |
| $-CO_2CH_2CH_2Br$ | H |
| $-CO_2CH_2CCl_3$ | H |
| $-CO_2CH_2CHCl_2$ | 4-$CH_3$ |
| $-CO_2CH_2CH_2OCH_3$ | H |
| $-CO_2CH_2CH_2OCH_2CH_3$ | H |
| $-CO_2CH_2CH_2CH_2OCH_3$ | H |
| $-SO_2CH_3$ | 7-Br |
| $-SO_2C_2H_5$ | H |
| $-SO_2CH(CH_3)_2$ | H |
| $-SO_2(CH_2)_3H$ | H |
| $-SO_2(CH_2)_4H$ | 5-$NO_2$ |
| $-SO_2N(CH_3)_2$ | H |
| $-SO_2N(C_2H_5)_2$ | H |
| $SO_2NCH(CH_3)_2$<br>$\mid$<br>$CH_3$ | H |
| $-SO_2N(CH_3)OCH_3$ | 7-$OCH_3$ |

TABLE Ic

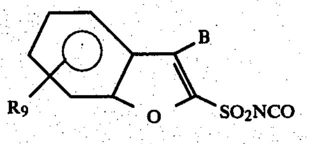

| B | $R_9$ |
|---|---|
| H | H |
| H | 4-Cl |
| $NO_2$ | H |
| $-CH_3$ | H |
| $-C_2H_5$ | 5-Br |
| Cl | H |
| Br | H |
| $-CH(CH_3)_2$ | H |
| $CH_3O-$ | 6-$OCH_3$ |
| $C_2H_5O-$ | H |
| $CH_3CH_2CH_2O-$ | H |
| $-CO_2CH_3$ | H |
| $-CO_2CH_3$ | 4-Cl |
| $-CO_2CH_3$ | 6-Cl |
| $-CO_2CH_3$ | 4-$NO_2$ |
| $-CO_2CH_3$ | 5-$NO_2$ |

TABLE Ic-continued

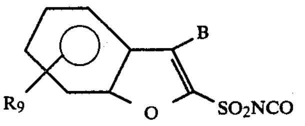

| B | $R_9$ |
|---|---|
| $-CO_2CH_3$ | 4-$OCH_3$ |
| $-CO_2CH_3$ | 5-$OCH_3$ |
| $-CO_2C_2H_5$ | H |
| $-CO_2CH(CH_3)_2$ | H |
| $-CO_2CH(CH_3)C_2H_5$ | H |
| $-CO_2CHCH{=}CH_2$ | 7-$CH_3$ |
| $-CO_2CH(CH_3)CH{=}CH_2$ | H |
| $-CO_2CHCHCH_3$ | H |
| $-CO_2CH_2CH_2Cl$ | 6-Br |
| $-CO_2CH_2CF_3$ | H |
| $-CO_2CH_2CH_2Br$ | H |
| $-CO_2CH_2CCl_3$ | H |
| $-CO_2CH_2CHCl_2$ | 4-$CH_3$ |
| $-CO_2CH_2CH_2OCH_3$ | H |
| $-CO_2CH_2CH_2OCH_2CH_3$ | H |
| $-CO_2CH_2CH_2CH_2OCH_3$ | H |
| $-SO_2CH_3$ | 7-Br |
| $-SO_2C_2H_5$ | H |
| $-SO_2CH(CH_3)_2$ | H |
| $-SO_2(CH_2)_3H$ | H |
| $-SO_2(CH_2)_4H$ | 5-$NO_2$ |
| $-SO_2N(CH_3)_2$ | H |
| $-SO_2N(C_2H_5)_2$ | H |
| $SO_2NCH(CH_3)_2$ with $CH_3$ on N | H |
| $-SO_2N(CH_3)OCH_3$ | 7-$OCH_3$ |

EXAMPLE 3

Methyl 3-(chlorosulfonyl)benzothiophene-3-carboxylate

To 28.5 g of methyl 3-aminobenzothiophene-2-carboxylate in 100 ml of glacial acetic acid and 33 ml of 12 N. hydrochloric acid in admixture was heated at 0° C. (±5°) dropwise 11.0 g of sodium nitrite in 30 ml of water. After stirring at 0° C. for 1 hour the above solution was added at 0° to a mixture containing 90 ml of acetic acid 40 g of sulfur dioxide, 5 g of cupric chloride and 90 ml of ethyl ether. After stirring overnight at 0° C. the mixture was filtered to yield 15 g of a solid m.p. 102°-104° which showed a mole weight of 290 by mass spectrum analysis, consistent for the desired compound. Extraction of the filtrate with methylene chloride followed by evaporation of the methylene chloride yielded an oil which contained an additional amount of the desired compound.

Alternatively sulfonyl chlorides can be prepared as described in Equations 4 and 5.

The sulfonyl chloride derivatives of tables II-IIc can be prepared from the appropriately substituted benzofuran or benzothiophene according to the methods set forth in Equations 4 and 5 or Example 3.

TABLE II

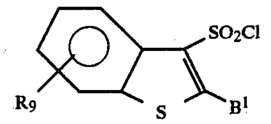

| $B^1$ | $R_9$ | m.p. °C. |
|---|---|---|
| $CO_2CH_3$ | H | 102-104 |
| $NO_2$ | H | |
| $-C_2H_5$ | 5-Br | |
| Cl | H | |
| Br | H | |
| $-CH(CH_3)_2$ | H | |
| $CH_3O-$ | 6-$OCH_3$ | |
| $C_2H_5O-$ | H | |
| $CH_3CH_2CH_2O-$ | H | |
| $-CO_2CH_3$ | 4-Cl | |
| $-CO_2CH_3$ | 6-Cl | |
| $-CO_2CH_3$ | 4-$NO_2$ | |
| $-CO_2CH_3$ | 5-$NO_2$ | |
| $-CO_2CH_3$ | 4-$OCH_3$ | |
| $-CO_2CH_3$ | 5-$OCH_3$ | |
| $-CO_2C_2H_5$ | H | |
| $-CO_2CH(CH_3)_2$ | H | |
| $-CO_2CH(CH_3)C_2H_5$ | H | |
| $-CO_2CHCH{=}CH_2$ | 7-$CH_3$ | |
| $-CO_2CH(CH_3)CH{=}CH_2$ | H | |
| $-CO_2CHCHCH_3$ | H | |
| $-CO_2CH_2CH_2Cl$ | 6-Br | |
| $-CO_2CH_2CF_3$ | H | |
| $-CO_2CH_2CH_2Br$ | H | |
| $-CO_2CH_2CCl_3$ | H | |
| $-CO_2CH_2CHCl_2$ | 4-$CH_3$ | |
| $-CO_2CH_2CH_2OCH_3$ | H | |
| $-CO_2CH_2CH_2OCH_2CH_3$ | H | |
| $-CO_2CH_2CH_2CH_2OCH_3$ | H | |
| $-SO_2CH_3$ | 7-Br | |
| $-SO_2C_2H_5$ | H | |
| $-SO_2CH(CH_3)_2$ | H | |
| $-SO_2(CH_2)_3H$ | H | |
| $-SO_2(CH_2)_4H$ | 5-$NO_2$ | |
| $-SO_2N(CH_3)_2$ | H | |
| $-SO_2N(C_2H_5)_2$ | H | |
| $-SO_2N(CH_3)OCH_3$ | 7-$OCH_3$ | |
| $SO_2NCH(CH_3)_2$ with $CH_3$ on N | H | |
| $CON(CH_3)_2$ | H | |
| $CON(C_2H_5)_2$ | H | |
| $CON(CH_3)CH(CH_3)_2$ | H | |
| $CON(CH_3)OCH_3$ | H | |

TABLE IIa

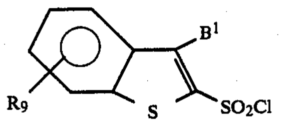

| $B^1$ | $R_9$ |
|---|---|
| $CO_2CH_3$ | H |
| $NO_2$ | H |
| $-C_2H_5$ | 5-Br |
| Cl | H |
| Br | H |
| $-CH(CH_3)_2$ | H |
| $CH_3O-$ | 6-$OCH_3$ |
| $C_2H_5O-$ | H |
| $CH_3CH_2CH_2O-$ | H |
| $-CO_2CH_3$ | 4-Cl |
| $-CO_2CH_3$ | 6-Cl |
| $-CO_2CH_3$ | 4-$NO_2$ |
| $-CO_2CH_3$ | 5-$NO_2$ |
| $-CO_2CH_3$ | 4-$OCH_3$ |
| $-CO_2CH_3$ | 5-$OCH_3$ |

TABLE IIa-continued

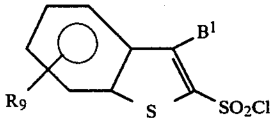

| $B^1$ | $R_9$ |
|---|---|
| $-CO_2C_2H_5$ | H |
| $-CO_2CH(CH_3)_2$ | H |
| $-CO_2CH(CH_3)C_2H_5$ | H |
| $-CO_2CHCH{=}CH_2$ | 7-$CH_3$ |
| $-CO_2CH(CH_3)CH{=}CH_2$ | H |
| $-CO_2CHCHCH_3$ | H |
| $-CO_2CH_2CH_2Cl$ | 6-Br |
| $-CO_2CH_2CF_3$ | H |
| $-CO_2CH_2CH_2Br$ | H |
| $-CO_2CH_2CCl_3$ | H |
| $-CO_2CH_2CHCl_2$ | 4-$CH_3$ |
| $-CO_2CH_2CH_2OCH_3$ | H |
| $-CO_2CH_2CH_2OCH_2CH_3$ | H |
| $-CO_2CH_2CH_2CH_2OCH_3$ | H |
| $-SO_2CH_3$ | 7-Br |
| $-SO_2C_2H_5$ | H |
| $-SO_2CH(CH_3)_2$ | H |
| $-SO_2(CH_2)_3H$ | H |
| $-SO_2(CH_2)_4H$ | 5-$NO_2$ |
| $-SO_2N(CH_3)_2$ | H |
| $-SO_2N(C_2H_5)_2$ | H |
| $-SO_2N(CH_3)OCH_3$ | 7-$OCH_3$ |
| $SO_2NCH(CH_3)_2$<br>$CH_3$ | H |
| $CON(CH_3)_2$ | H |
| $CON(CH_3CH_2)$ | H |
| $CON(CH_3)CH(CH_3)_2$ | H |
| $CON(CH_3)OCH_3$ | H |

TABLE IIb

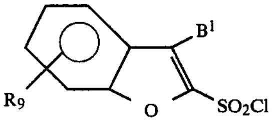

| $B^1$ | $R_9$ |
|---|---|
| $CO_2CH_3$ | H |
| $NO_2$ | H |
| $-C_2H_5$ | 5-Br |
| Cl | H |
| Br | H |
| $-CH(CH_3)_2$ | H |
| $CH_3O-$ | 6-$OCH_3$ |
| $C_2H_5O-$ | H |
| $CH_3CH_2CH_2O-$ | H |
| $-CO_2CH_3$ | 4-Cl |
| $-CO_2CH_3$ | 6-Cl |
| $-CO_2CH_3$ | 4-$NO_2$ |
| $-CO_2CH_3$ | 5-$NO_2$ |
| $-CO_2CH_3$ | 4-$OCH_3$ |
| $-CO_2CH_3$ | 5-$OCH_3$ |
| $-CO_2C_2H_5$ | H |
| $-CO_2CH(CH_3)_2$ | H |
| $-CO_2CH(CH_3)C_2H_5$ | H |
| $-CO_2CHCH{=}CH_2$ | 7-$CH_3$ |
| $-CO_2CH(CH_3)CH{=}CH_2$ | H |
| $-CO_2CHCHCH_3$ | H |
| $-CO_2CH_2CH_2Cl$ | 6-Br |
| $-CO_2CH_2CF_3$ | H |
| $-CO_2CH_2CH_2Br$ | H |
| $-CO_2CH_2CCl_3$ | H |
| $-CO_2CH_2CHCl_2$ | 4-$CH_3$ |
| $-CO_2CH_2CH_2OCH_3$ | H |
| $-CO_2CH_2CH_2OCH_2CH_3$ | H |
| $-CO_2CH_2CH_2CH_2OCH_3$ | H |
| $-SO_2CH_3$ | 7-Br |

TABLE IIb-continued

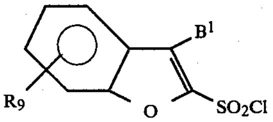

| $B^1$ | $R_9$ |
|---|---|
| $-SO_2C_2H_5$ | H |
| $-SO_2CH(CH_3)_2$ | H |
| $-SO_2(CH_2)_3H$ | H |
| $-SO_2(CH_2)_4H$ | 5-$NO_2$ |
| $-SO_2N(CH_3)_2$ | H |
| $-SO_2N(C_2H_5)_2$ | H |
| $-SO_2N(CH_3)OCH_3$ | 7-$OCH_3$ |
| $SO_2NCH(CH_3)_2$<br>$CH_3$ | H |
| $CON(CH_3)_2$ | H |
| $CON(C_2H_5)_2$ | H |
| $CON(CH_3)CH(CH_3)_2$ | H |
| $CON(CH_3)OCH_3$ | H |

TABLE IIc

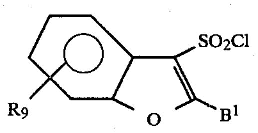

| $B^1$ | $R_9$ |
|---|---|
| $CO_2CH_3$ | H |
| $NO_2$ | H |
| $-C_2H_5$ | 5-Br |
| Cl | H |
| Br | H |
| $-CH(CH_3)_2$ | H |
| $CH_3O-$ | 6-$OCH_3$ |
| $C_2H_5O-$ | H |
| $CH_3CH_2CH_2O-$ | H |
| $-CO_2CH_3$ | 4-Cl |
| $-CO_2CH_3$ | 6-Cl |
| $-CO_2CH_3$ | 4-$NO_2$ |
| $-CO_2CH_3$ | 5-$NO_2$ |
| $-CO_2CH_3$ | 4-$OCH_3$ |
| $-CO_2CH_3$ | 5-$OCH_3$ |
| $-CO_2C_2H_5$ | H |
| $-CO_2CH(CH_3)_2$ | H |
| $-CO_2CH(CH_3)C_2H_5$ | H |
| $-CO_2CHCH{=}CH_2$ | 7-$CH_3$ |
| $-CO_2CH(CH_3)CH{=}CH_2$ | H |
| $-CO_2CHCHCH_3$ | H |
| $-CO_2CH_2CH_2Cl$ | 6-Br |
| $-CO_2CH_2CF_3$ | H |
| $-CO_2CH_2CH_2Br$ | H |
| $-CO_2CH_2CCl_3$ | H |
| $-CO_2CH_2CHCl_2$ | 4-$CH_3$ |
| $-CO_2CH_2CH_2OCH_3$ | H |
| $-CO_2CH_2CH_2OCH_2CH_3$ | H |
| $-CO_2CH_2CH_2CH_2OCH_3$ | H |
| $-SO_2CH_3$ | 7-Br |
| $-SO_2C_2H_5$ | H |
| $-SO_2CH(CH_3)_2$ | H |
| $-SO_2(CH_2)_3H$ | H |
| $-SO_2(CH_2)_4H$ | 5-$NO_2$ |
| $-SO_2N(CH_3)_2$ | H |
| $-SO_2N(C_2H_5)_2$ | H |
| $-SO_2N(CH_3)OCH_3$ | 7-$OCH_3$ |
| $SO_2NCH(CH_3)_2$<br>$CH_3$ | H |
| $CON(CH_3)_2$ | H |
| $CON(C_2H_5)_2$ | H |
| $CON(CH_3)CH(CH_3)_2$ | H |

TABLE IIc-continued

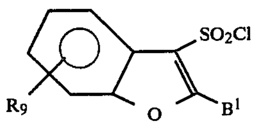

| $B^1$ | $R_9$ |
|---|---|
| $CON(CH_3)OCH_3$ | H |

EXAMPLE 4

Methyl 3-Sulfamoylbenzothiophene-2-carboxylate

A solution of 20.8 g of methyl 3-chlorosulfamoyl benzothiophene-2-carboxylate in 500 ml of dichloromethane was cooled to 0° C. and treated with 5.0 ml of liquid ammonia. The cooling bath was removed, the mixture stirred for 1 hour at ambient temperature and poured into ice. The mixture was acidified, dichloromethane extracted, the extract washed with water and brine, dried over magnesium sulfate, filtered and concentrated in vacuo. The resulting solid was suspended in n-butyl chloride and filtered to give 17.0 g of the desired sulfonamide, m.p. 172°-175° C. IR: 3300 and 3200 ($NH_2$), 1695 (CO), 1385 and 1750 ($SO_2$) $cm^{-1}$ 60MC NMR ($CDCl_3$) δ9.0-7.2 (m, aromatic protons), 6.0 (brs. 2H, $NH_2$), 3.9 (s, 3H, $CH_3$).

The appropriately substituted sulfonamides which are useful for preparing the herbicides disclosed in this application can be prepared from the sulfonyl chlorides exemplified in tables II-IIc by the method set forth in Example 4. The substitution pattern thus obtained is the same as it was for the sulfonyl chloride intermediates. These are listed in tables III-IIIc.

EXAMPLE 5

N-tert-Butylbenzothiophene-3-sulfonamide

To 25 g of tert-butyl amine in 100 ml of dry tetrahydrofuran was added dropwise with cooling 34 g of benzothiophene-3-sulfonyl chloride. The reaction mixture was allowed to come to room temperature and then poured into 200 g of ice. The phases were separated and the organic portion was washed with water, dried over magnesium sulfate and evaporated in vacuo. The residue thus obtained melted at 146°-148° after recrystallization from alcohol. It showed an absorption peak by NMR at 1.34 δ (singlet), for tert-butyl and 7.4-8.4 δ (multiplet) for benzothiophene consistent for the desired product.

EXAMPLE 6

3-tert-Butylaminosulfonylbenzothiophene-2-carboxylic acid

N-tert-Butylbenzothiophene-3-sulfonamide (13.6 g) and 400 ml of anhydrous tetrahydrofuran in admixture were cooled to 0° and 120 ml of butyl lithium in hexane (1.6 molar) was added cautiously, dropwise. After the addition was completed the mixture was stirred at room temperature for 2 hours and carbon dioxide was then passed into the system for two hours while cooling to 15°. Two hundred ml of water was then cautiously added followed by 40 ml of 12 N hydrochloric acid. The solution was then evaporated to half of its original volume, extracted with methylene chloride and the organic phase washed with water, dried over magnesium sulfate, filtered and evaporated to dryness to yield a white solid of m.p. 180° with gas evolution. Nuclear Magnetic Resonance spectroscopy showed the t-butyl absorption at 1.3 δ (singlet) and benzothiophene hydrogen absorption at 7.4-8.0 (multiplet).

EXAMPLE 7

Methyl 3-Aminosulfonylbenzothiophene-2-carboxylate

A solution of 6 g of 3-tert-butylaminosulfonylbenzothiophene-2-carboxylate acid in 100 ml of methanol was saturated with anhydrous hydrogen chloride and then heated to reflux for three hours. The mixture was evaporated in vacuo to half of its volume and the residue poured into 200 g of ice and filtered to yield the desired product melting at 150°-154°. The infrared absorption spectrum shown by this material was qualitatively equivalent to that of the product of Example 4.

TABLE III

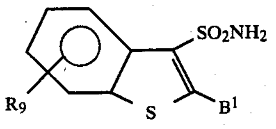

| $B^1$ | $R_9$ | m.p. °C. |
|---|---|---|
| $CO_2CH_3$ | H | 172-175 |
| $NO_2$ | H | |
| $-C_2H_5$ | 5-Br | |
| Cl | H | |
| Br | H | |
| $-CH(CH_3)_2$ | H | |
| $CH_3O-$ | 6-$OCH_3$ | |
| $C_2H_5O-$ | H | |
| $CH_3CH_2CH_2O-$ | H | |
| $-CO_2CH_3$ | 4-Cl | |
| $-CO_2CH_3$ | 6-Cl | |
| $-CO_2CH_3$ | 4-$NO_2$ | |
| $-CO_2CH_3$ | 5-$NO_2$ | |
| $-CO_2CH_3$ | 4-$OCH_3$ | |
| $-CO_2CH_3$ | 5-$OCH_3$ | |
| $-CO_2C_2H_5$ | H | |
| $-CO_2CH(CH_3)_2$ | H | |
| $-CO_2CH(CH_3)C_2H_5$ | H | |
| $-CO_2CHCH{=}CH_2$ | 7-$CH_3$ | |
| $-CO_2CH(CH_3)CH{=}CH_2$ | H | |
| $-CO_2CHCHCH_3$ | H | |
| $-CO_2CH_2CH_2Cl$ | 6-Br | |
| $-CO_2CH_2CF_3$ | H | |
| $-CO_2CH_2CH_2Br$ | H | |
| $-CO_2CH_2CCl_3$ | H | |
| $-CO_2CH_2CHCl_2$ | 4-$CH_3$ | |
| $-CO_2CH_2CH_2OCH_3$ | H | |
| $-CO_2CH_2CH_2OCH_2CH_3$ | H | |
| $-CO_2CH_2CH_2CH_2OCH_3$ | H | |
| $-SO_2CH_3$ | 7-Br | |
| $-SO_2C_2H_5$ | H | |
| $-SO_2CH(CH_3)_2$ | H | |
| $-SO_2(CH_2)_3H$ | H | |
| $-SO_2(CH_2)_4H$ | 5-$NO_2$ | |
| $-SO_2N(CH_3)_2$ | H | |
| $-SO_2N(C_2H_5)_2$ | H | |
| $-SO_2N(CH_3)OCH_3$ | 7-$OCH_3$ | |
| $SO_2N(CH_3)CH(CH_3)_2$ | H | |
| $CON(CH_3)_2$ | H | |
| $CON(C_2H_5)_2$ | H | |
| $CON(CH_3)CH(CH_3)_2$ | H | |
| $CON(CH_3)OCH_3$ | H | |

TABLE IIIa

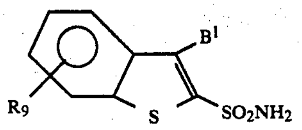

| $B^1$ | $R_9$ |
|---|---|
| $CO_2CH_3$ | H |
| $NO_2$ | H |
| $-C_2H_5$ | 5-Br |
| Cl | H |
| Br | H |
| $-CH(CH_3)_2$ | H |
| $CH_3O-$ | 6-$OCH_3$ |
| $C_2H_5O-$ | H |
| $CH_3CH_2CH_2O-$ | H |
| $-CO_2CH_3$ | 4-Cl |
| $-CO_2CH_3$ | 6-Cl |
| $-CO_2CH_3$ | 4-$NO_2$ |
| $-CO_2CH_3$ | 5-$NO_2$ |
| $-CO_2CH_3$ | 4-$OCH_3$ |
| $-CO_2CH_3$ | 5-$OCH_3$ |
| $-CO_2C_2H_5$ | H |
| $-CO_2CH(CH_3)_2$ | H |
| $-CO_2CH(CH_3)C_2H_5$ | H |
| $-CO_2CHCH{=}CH_2$ | 7-$CH_3$ |
| $-CO_2CH(CH_3)CH{=}CH_2$ | H |
| $-CO_2CHCHCH_3$ | H |
| $-CO_2CH_2CH_2Cl$ | 6-Br |
| $-CO_2CH_2CF_3$ | H |
| $-CO_2CH_2CH_2Br$ | H |
| $-CO_2CH_2CCl_3$ | H |
| $-CO_2CH_2CHCl_2$ | 4-$CH_3$ |
| $-CO_2CH_2CH_2OCH_3$ | H |
| $-CO_2CH_2CH_2OCH_2CH_3$ | H |
| $-CO_2CH_2CH_2CH_2OCH_3$ | H |
| $-SO_2CH_3$ | 7-Br |
| $-SO_2C_2H_5$ | H |
| $-SO_2CH(CH_3)_2$ | H |
| $-SO_2(CH_2)_3H$ | H |
| $-SO_2(CH_2)_3H$ | 5-$NO_2$ |
| $-SO_2N(CH_3)_2$ | H |
| $-SO_2N(C_2H_5)_2$ | H |
| $-SO_2N(CH_3)OCH_3$ | 7-$OCH_3$ |
| $SO_2NCH(CH_3)_2$<br>\|<br>$CH_3$ | H |
| $CON(CH_3)_2$ | H |
| $CON(CH_3CH_2)$ | H |
| $CON(CH_3)CH(CH_3)_2$ | H |
| $CON(CH_2)OCH_3$ | H |

TABLE IIIb

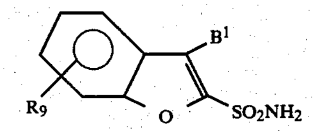

| $B^1$ | $R_9$ |
|---|---|
| $CO_2CH_3$ | H |
| $NO_2$ | H |
| $-C_2H_5$ | 5-Br |
| Cl | H |
| Br | H |
| $-CH(CH_3)_2$ | H |
| $CH_3O-$ | 6-$OCH_3$ |
| $C_2H_5O-$ | H |
| $CH_3CH_2CH_2O-$ | H |
| $-CO_2CH_3$ | 4-Cl |
| $-CO_2CH_3$ | 6-Cl |
| $-CO_2CH_3$ | 4-$NO_2$ |
| $-CO_2CH_3$ | 5-$NO_2$ |
| $-CO_2CH_3$ | 4-$OCH_3$ |
| $-CO_2CH_3$ | 5-$OCH_3$ |

TABLE IIIb-continued

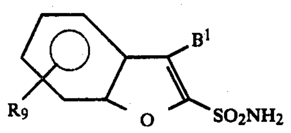

| $B^1$ | $R_9$ |
|---|---|
| $-CO_2C_2H_5$ | H |
| $-CO_2CH(CH_3)_2$ | H |
| $-CO_2CH(CH_3)C_2H_5$ | H |
| $-CO_2CHCH{=}CH_2$ | 7-$CH_3$ |
| $-CO_2CH(CH_3)CH{=}CH_2$ | H |
| $-CO_2CHCHCH_3$ | H |
| $-CO_2CH_2CH_2Cl$ | 6-Br |
| $-CO_2CH_2CF_3$ | H |
| $-CO_2CH_2CH_2Br$ | H |
| $-CO_2CH_2CCl_3$ | H |
| $-CO_2CH_2CHCl_2$ | 4-$CH_3$ |
| $-CO_2CH_2CH_2OCH_3$ | H |
| $-CO_2CH_2CH_2OCH_2CH_3$ | H |
| $-CO_2CH_2CH_2CH_2OCH_3$ | H |
| $-SO_2CH_3$ | 7-Br |
| $-SO_2C_2H_5$ | H |
| $-SO_2CH(CH_3)_2$ | H |
| $-SO_2(CH_2)_3H$ | H |
| $-SO_2(CH_2)_4H$ | 5-$NO_2$ |
| $-SO_2N(CH_3)_2$ | H |
| $-SO_2N(C_2H_5)_2$ | H |
| $-SO_2N(CH_3)OCH_3$ | 7-$OCH_3$ |
| $SO_2NCH(CH_3)_2$<br>\|<br>$CH_3$ | H |
| $CON(CH_3)_2$ | H |
| $CON(C_2H_5)_2$ | H |
| $CON(CH_3)CH(CH_3)_2$ | H |
| $CON(CH_3)OCH_3$ | H |

TABLE IIIc

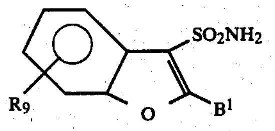

| $B^1$ | $R_9$ |
|---|---|
| $CO_2CH_3$ | H |
| $NO_2$ | H |
| $-C_2H_5$ | 5-Br |
| Cl | H |
| Br | H |
| $-CH(CH_3)_2$ | H |
| $CH_3O-$ | 6-$OCH_3$ |
| $C_2H_5O-$ | H |
| $CH_3CH_2CH_2O-$ | H |
| $-CO_2CH_3$ | 4-Cl |
| $-CO_2CH_3$ | 6-Cl |
| $-CO_2CH_3$ | 4-$NO_2$ |
| $-CO_2CH_3$ | 5-$NO_2$ |
| $-CO_2CH_3$ | 4-$OCH_3$ |
| $-CO_2CH_3$ | 5-$OCH_3$ |
| $-CO_2C_2H_5$ | H |
| $-CO_2CH(CH_3)_2$ | H |
| $-CO_2CH(CH_3)C_2H_5$ | H |
| $-CO_2CHCH{=}CH_2$ | 7-$CH_3$ |
| $-CO_2CH(CH_3)CH{=}CH_2$ | H |
| $-CO_2CHCHCH_3$ | H |
| $-CO_2CH_2CH_2Cl$ | 6-Br |
| $-CO_2CH_2CF_3$ | H |
| $-CO_2CH_2CH_2Br$ | H |
| $-CO_2CH_2CCl_3$ | H |
| $-CO_2CH_2CHCl_2$ | 4-$CH_3$ |
| $-CO_2CH_2CH_2OCH_3$ | H |
| $-CO_2CH_2CH_2OCH_2CH_3$ | H |
| $-CO_2CH_2CH_2CH_2OCH_3$ | H |
| $-SO_2CH_3$ | 7-Br |

TABLE IIIc-continued

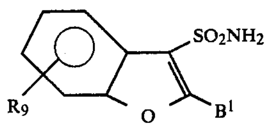

| $B^1$ | $R_9$ |
|---|---|
| $-SO_2C_2H_5$ | H |
| $-SO_2CH(CH_3)_2$ | H |
| $-SO_2(CH_2)_3H$ | H |
| $-SO_2(CH_2)_4H$ | 5-$NO_2$ |
| $-SO_2N(CH_3)_2$ | H |
| $-SO_2N(C_2H_5)_2$ | H |
| $-SO_2N(CH_3)OCH_3$ | 7-$OCH_3$ |
| $SO_2NCH(CH_3)_2$ with $CH_3$ on N | H |
| $CON(CH_3)_2$ | H |
| $CON(C_2H_5)_2$ | H |
| $CON(CH_3)CH(CH_3)_2$ | H |
| $CON(CH_3)OCH_3$ | H |

EXAMPLE 8

N-[(4-methoxy-6-methylpyrimidin-2-yl)aminocarbonyl]benzothiophene-3-sulfonamide

To 25 ml of anhydrous acetonitrile containing 1.4 g of 2-amino-4-methoxy-6-methylpyrimidine was added 2.4 g of benzothiophene-3-sulfonyl isocyanate with stirring. The mixture was heated to boiling, allowed to cool to room temperature and then stirred overnight. The resultant precipitate was filtered off and washed with ether to yield 2 g of the desired product, m.p. 180°-181° C. It showed absorption by NMR (60 MC) at 2.24 δ (6-$CH_3$ group), 3.8 δ (4-$OCH_3$), 6.2 δ (5-H on pyrimidine); 7-8 δ (aryl H's on benzo) and 8.3 δ (H on thiophene portion).

Anal. Calcd. for $C_{15}H_{14}N_4O_4S_2$: C, 47.61; H, 3.77; N, 14.81. Found: C, 47.59; H, 3.88; N, 14.83.

EXAMPLE 9

N-[(4-methoxy-6-methyl-1,3,5-triazin-2-yl)aminocarbonyl]benzothiophene-3-sulfonamide To 1.4 g of 2-amino-4-methoxy-6-methyl-1,3,5-triazine in 25 ml acetonitrile was added 2.4 g of benzothiophene-3-sulfonyl isocyanate with stirring. After stirring overnight at ambient temperature the mixture was filtered and the precipitate was washed with butyl chloride to yield 2.8 g of a white solid, m.p. 187°-188°. It showed absorption peaks by Nuclear Magnetic Resonance (60 MC) at 2.25 and 3.9 (methyl and methoxy in triazine), at 7-8 (benzo hydrogens) and 8.3 δ (thiophene hydrogen) consistent for the desired product.

EXAMPLE 10

N-[(4,6-Dimethoxy-1,3,5-triazin-2-yl)aminocarbonyl]-benzothiophene-3-sulfonamide Using the procedure of Example 3, and substituting 1.6 g of 2-amino-4,6-dimethoxy-1,3,5-triazine and 2.4 g of benzothiophene-3-sulfonyl isocyanate, a yield of 3.4 g of the desired product was obtained melting at 152°. It showed absorption peaks by Nuclear Magnetic Resonance (60 MC) at; 3.95 δ ($CH_3O$), 7-8 δ (benzohydrogens) and 8.3 δ (thiophene hydrogen) consistent for the desired compound.

EXAMPLE 11

N-[(4,6-Dimethylpyrimidin-2-yl)aminocarbonyl]benzofuransulfonamide, mixture of 2- and 3-positional isomers A suspension of 2.59 g of 2-amino-4,6-dimethylpyrimidine in 50 ml of nitromethane was cooled to −10° C. and treated with 2.0 ml of chlorosulfonyl isocyanate. After stirring for 0.5 hour at −10° C. a solution of 2.0 ml of benzofuran in 10 ml of nitromethane was added dropwise followed by 2.8 g of aluminum chloride. The mixture was stirred and heated at reflux until TLC monitoring indicated the disappearance of starting material. The mixture was cooled, poured into water, extracted with methylene chloride, the extract washed with water, dried over magnesium sulfate, filtered and concentrated in vacuo to a dark oil. Trituration with dichloromethane followed by washing with acetonitrile gave the desired product as a mixture of 2- and 3-positional isomers, m.p. 206°-218° C. dec. The product exhibited IR bands at 3300 (NH), 1710 (C=O, 1340 ($SO_2$) and 1140 ($SO_2$) $cm^{-1}$ and NMR absorptions at δ 2.4 (s, pyrimidine methyls) and 6.3-8.0 (m, aromatic and pyrimidine H's).

By using the procedures of Examples 8 through 11 with the appropriately substituted benzothiophene or benzofuran and heterocyclic amine the compounds of Tables IV-IVc, V-Vc and Tables VI-VIc can be prepared. Alternatively, the methods described in Equations 8a-8c can be used for the synthesis of some of these compounds as will be understood by one skilled in the art.

TABLE IV

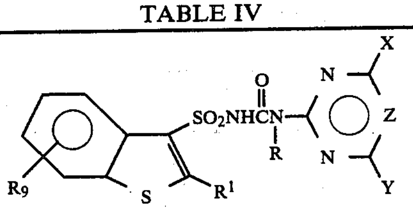

| $R^1$ | $R_9$ | R | X | Y | Z | m.p. (°C.) |
|---|---|---|---|---|---|---|
| H | H | H | $CH_3$ | $CH_3$ | CH | 187-191° |
| H | H | H | $OCH_3$ | $OCH_3$ | CH | 152° |
| H | H | H | $CH_3$ | $CH_3$ | N | |
| $CH_3$ | 7-Cl | H | $CH_3$ | $OCH_3$ | CH | |
| $CH_3$ | H | H | $CH_3$ | $CH_3$ | CH | |
| $CH_3$ | H | H | $OCH_3$ | $OCH_3$ | CH | |
| $CH(CH_3)_2$ | H | H | $OCH_3$ | $CH_3$ | CH | |
| $CH(CH_3)_2$ | H | H | $OCH_3$ | $CH_3$ | N | |
| $C_2H_5$ | H | H | $OCH_3$ | $OCH_3$ | CN | |

TABLE IV-continued

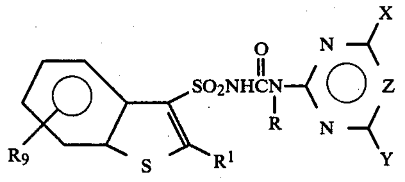

| $R^1$ | $R_9$ | R | X | Y | Z | m.p. (°C.) |
|---|---|---|---|---|---|---|
| $SO_2(CH_2)_4H$ | H | H | $OCH_3$ | $CH_3$ | N | |
| $SO_2N(CH_3)_2$ | H | H | $CH_3$ | $CH_3$ | CH | |
| $SO_2N(CH_3)_2$ | H | H | $CH_3$ | $OCH_3$ | CH | |
| $SO_2N(CH_3)_2$ | H | H | $OCH_3$ | $OCH_3$ | CH | |
| $SO_2N(CH_3)_2$ | H | H | $CH_3$ | $CH_3$ | N | |
| $SO_2N(CH_3)_2$ | H | H | $CH_3$ | $OCH_3$ | N | |
| $SO_2N(CH_3)_2$ | H | H | $OCH_3$ | $OCH_3$ | N | |
| $SO_2N(CH_3)_2$ | H | $CH_3$ | $OCH_3$ | $OCH_3$ | N | |
| $SO_2N(C_2H_5)_2$ | H | H | $OCH_3$ | $OCH_3$ | N | |
| $SO_2N(C_2H_5)_2$ | 5-$CH_3$ | H | $OCH_3$ | $OCH_3$ | CH | |
| $SO_2N(CH_3)C_2H_5$ | H | H | $CH_3$ | $OCH_3$ | CH | |
| $CO_2CH_3$ | H | H | H | $CH_3$ | N | |
| $CO_2CH_3$ | H | H | $OC_2H_5$ | $OC_2H_5$ | N | |
| $CO_2CH_3$ | H | H | $OC_2H_5$ | $OC_2H_5$ | CH | |
| $CO_2CH_3$ | H | H | $OCH_2CF_3$ | $OCH_3$ | CH | |
| $CO_2CH_3$ | H | H | $CH_2OCH_3$ | $OCH_3$ | N | |
| $CO_2CH_3$ | H | H | $CH_2OCH_3$ | $CH_3$ | N | |
| $CO_2CH_3$ | H | $CH_3$ | $OCH_3$ | $OCH_3$ | CH | |
| $CO_2CH_3$ | H | H | Cl | Cl | N | |
| $CO_2C_2H_5$ | H | H | $CH_3$ | $CH_3$ | CH | |
| $CO_2C_2H_5$ | H | H | $CH_3$ | $OCH_3$ | CH | |
| $CO_2C_2H_5$ | H | H | $OCH_3$ | $OCH_3$ | CH | |
| $CO_2C_2H_5$ | H | H | $CH_3$ | $CH_3$ | N | |
| $CO_2C_2H_5$ | H | H | $CH_3$ | $OCH_3$ | N | |
| $CO_2C_2H_5$ | H | H | $OCH_3$ | $OCH_3$ | N | |
| $CO_2C_2H_5$ | H | $CH_3$ | $OCH_3$ | $OCH_3$ | N | |
| $CO_2(CH_2)_3H$ | H | H | $OCH_3$ | $OCH_3$ | CH | |
| $CO_2(CH_2)_3H$ | H | H | $CH_3$ | $OCH_3$ | N | |
| $CON(CH_3)_2$ | H | H | $CH_3$ | $OCH_3$ | N | |
| $CON(CH_3)_2$ | H | H | $CH_3$ | $CH_3$ | CH | |
| $CON(CH_3)_2$ | H | H | $OCH_3$ | $OCH_3$ | CH | |
| $CON(CH_3)_2$ | H | H | $CH_3$ | $OCH_3$ | CH | |
| $CON(CH_3)_2$ | H | H | $CH_3$ | $CH_3$ | N | |
| $CON(CH_3)_2$ | H | H | $OCH_3$ | $OCH_3$ | N | |
| $CON(CH_3)_2$ | H | $CH_3$ | $OCH_3$ | $OCH_3$ | N | |
| $CON(C_2H_5)_2$ | 7-Cl | H | $OCH_3$ | $CH_3$ | N | |
| $CON(CH_3)CH(CH_3)_2$ | H | H | $CH_3$ | $CH_3$ | CH | |
| 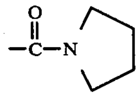 | H | H | $OCH_3$ | $CH_3$ | N | |
| $SO_2N(CH_3)CH(CH_3)_2$ | H | H | $CH_3$ | $CH_3$ | CH | |
| $SO_2N(CH_3)(CH_2)_3H$ | H | H | $OCH_3$ | $OCH_3$ | CH | |
| $CO_2CH_3$ | H | H | $CH_3$ | Cl | N | |
| $CO_2CH_3$ | H | H | $OCH_3$ | Cl | N | |
| $CO_2CH_3$ | H | H | $OCH_2CF_3$ | Cl | N | |
| $SO_2N(CH_3)OCH_3$ | H | H | $CH_3$ | $CH_3$ | CH | |
| $SO_2N(CH_3)OCH_3$ | H | H | $CH_3$ | $OCH_3$ | CH | |
| $SO_2N(CH_3)OCH_3$ | H | H | $OCH_3$ | $OCH_3$ | CH | |
| $SO_2N(CH_3)OCH_3$ | H | H | $CH_3$ | $CH_3$ | N | |
| $SO_2N(CH_3)OCH_3$ | H | H | $CH_3$ | $OCH_3$ | N | |
| $SO_2N(CH_3)OCH_3$ | H | H | $OCH_3$ | $OCH_3$ | N | |
| $SO_2N(CH_3)OCH_3$ | H | $CH_3$ | $OCH_3$ | $OCH_3$ | N | |

TABLE IV-continued

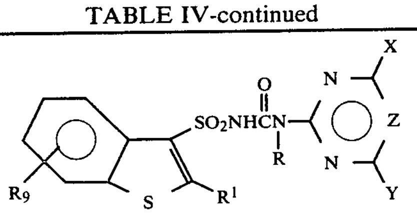

| R¹ | R₉ | R | X | Y | Z | m.p. (°C.) |
|---|---|---|---|---|---|---|
| $C_2H_5$ | 5-$NO_2$ | H | $CH_3$ | $OCH_3$ | N | |
| Cl | H | H | $CH_3$ | $OCH_3$ | N | |
| Cl | H | H | $CH_3$ | $CH_3$ | CH | |
| Cl | H | H | $CH_3$ | $CH_3$ | N | |
| Cl | H | H | $CH_3$ | $OCH_3$ | CH | |
| Cl | H | H | $OCH_3$ | $OCH_3$ | CH | |
| Cl | H | H | $OCH_3$ | $OCH_3$ | N | |
| Br | H | H | $OCH_3$ | $OCH_3$ | CH | |
| Br | 6-$CH_3$ | H | $OCH_3$ | $CH_3$ | N | |
| $OCH_3$ | H | H | $CH_3$ | $OCH_3$ | CH | |
| $OCH_3$ | H | H | $CH_3$ | $OCH_3$ | N | |
| $OC_2H_5$ | H | H | $OCH_3$ | $OCH_3$ | CH | |
| $O(CH_2)_3H$ | H | H | $OCH_3$ | $CH_3$ | CH | |
| $CO_2CH_3$ | H | H | $CH_3$ | $CH_3$ | CH | 207–208° |
| $CO_2CH_3$ | H | H | $CH_3$ | $OCH_3$ | CH | 108–111° |
| $CO_2CH_3$ | H | H | $OCH_3$ | $OCH_3$ | CH | 209–210° |
| H | H | H | $CH_3$ | $OCH_3$ | CH | 180–181° |
| H | H | H | $CH_3$ | $OCH_3$ | N | 187–188° |
| H | H | H | $OCH_3$ | $OCH_3$ | N | |
| $CO_2CH_3$ | H | H | $CH_3$ | $CH_3$ | N | 195–198° |
| $CO_2CH_3$ | H | H | $CH_3$ | $OCH_3$ | N | 185–195° |
| $CO_2CH_3$ | H | H | $OCH_3$ | $OCH_3$ | N | 193–195° |
| $CO_2CH_3$ | H | $CH_3$ | $OCH_3$ | $OCH_3$ | N | 160–162° |
| $CO_2CH_3$ | H | H | $CH_3$ | $OCH_3$ | CCl | |
| $CO_2CH_3$ | H | H | $CH_3$ | $CH_3$ | CCl | |
| $CO_2CH_3$ | H | H | $CH_3$ | $OCH_3$ | CBr | |
| $CO_2CH_3$ | H | H | $CH_3$ | $NH_2$ | CH | |
| $CO_2CH_3$ | H | H | $CH_3$ | $NHCH_3$ | CH | |
| $CO_2CH_3$ | H | H | $CH_3$ | $N(CH_3)_2$ | CH | |
| $CO_2CH_3$ | H | H | $CH_3$ | $SCH_3$ | CH | |
| $CO_2CH_3$ | 4-Cl | H | $CH_3$ | $CH_3$ | CH | |
| $CO_2CH_3$ | 4-Cl | H | $CH_3$ | $OCH_3$ | CH | |
| $CO_2CH_3$ | 4-Cl | H | $OCH_3$ | $OCH_3$ | CH | |
| $CO_2CH_3$ | 4-Cl | H | $CH_3$ | $CH_3$ | N | |
| $CO_2CH_3$ | 4-Cl | H | $CH_3$ | $OCH_3$ | N | |
| $CO_2CH_3$ | 4-Cl | H | $OCH_3$ | $OCH_3$ | N | |
| $CO_2CH_3$ | 4-Cl | $CH_3$ | $OCH_3$ | $OCH_3$ | N | |
| $CO_2CH_3$ | 4-$NO_2$ | H | $CH_3$ | $CH_3$ | CH | |
| $CO_2CH_3$ | 4-$NO_2$ | H | $CH_3$ | $OCH_3$ | CH | |
| $CO_2CH_3$ | 4-$NO_2$ | H | $OCH_3$ | $OCH_3$ | CH | |
| $CO_2CH_3$ | 4-$NO_2$ | H | $CH_3$ | $CH_3$ | N | |
| $CO_2CH_3$ | 4-$NO_2$ | H | $CH_3$ | $OCH_3$ | N | |
| $CO_2CH_3$ | 4-$NO_2$ | H | $OCH_3$ | $OCH_3$ | N | |
| $CO_2CH_3$ | 4-$NO_2$ | $CH_3$ | $OCH_3$ | $OCH_3$ | N | |
| $CO_2CH_3$ | H | H | $CH_3$ | $OCH_3$ | CBr | |
| $CO_2CH_3$ | H | H | $CH_3$ | $OCH_3$ | CCN | |
| $CO_2CH_3$ | 7-$OCH_3$ | H | $CH_3$ | $OCH_3$ | CCN | |
| $CO_2CH_3$ | H | H | $CH_3$ | $OCH_3$ | $CCH_3$ | |
| $CO_2CH_3$ | H | H | $CH_3$ | $OCH_3$ | $CC_2H_5$ | |
| $CO_2CH_3$ | H | H | $OCH_3$ | $OCH_3$ | $CCH_2CH_3$ | |
| $CO_2CH_3$ | H | H | $OCH_3$ | $OCH_3$ | $CCH_3$ | |
| $CO_2CH_3$ | H | H | $CH_3$ | $OCH_3$ | $CCH_2CH_2Cl$ | |
| $CO_2CH_3$ | H | H | $OCH_3$ | $OCH_3$ | $CCH_2CH_2Cl$ | |
| $CO_2CH_3$ | H | H | $CH_3$ | $OCH_3$ | $CCH_2CH{=}CH_2$ | |
| $CO_2CH_3$ | 6-Br | H | $CH_3$ | $OCH_3$ | $CCH_2CH{=}CH_2$ | |
| $SO_2CH_3$ | H | H | $CH_3$ | $CH_3$ | CH | |
| $SO_2CH_3$ | H | H | $CH_3$ | $OCH_3$ | CH | |
| $SO_2CH_3$ | H | H | $OCH_3$ | $OCH_3$ | CH | |
| $SO_2CH_3$ | H | H | $CH_3$ | $CH_3$ | N | |
| $SO_2CH_3$ | H | H | $CH_3$ | $OCH_3$ | N | |
| $SO_2CH_3$ | H | H | $OCH_3$ | $OCH_3$ | N | |
| $SO_2CH_3$ | H | $CH_3$ | $OCH_3$ | $OCH_3$ | N | |
| $SO_2C_2H_5$ | H | H | $CH_3$ | $CH_3$ | CH | |
| $SO_2C_2H_5$ | H | H | $CH_3$ | $OCH_3$ | CH | |
| $SO_2C_2H_5$ | H | H | $OCH_3$ | $OCH_3$ | CH | |
| $SO_2C_2H_5$ | H | H | $CH_3$ | $CH_3$ | N | |
| $SO_2C_2H_5$ | H | H | $CH_3$ | $OCH_3$ | N | |
| $SO_2C_2H_5$ | H | H | $OCH_3$ | $OCH_3$ | N | |
| $SO_2C_2H_5$ | H | $CH_3$ | $OCH_3$ | $OCH_3$ | N | |
| $SO_2CH(CH_3)_2$ | H | H | $CH_3$ | $CH_3$ | CH | |
| $SO_2(CH_2)_3H$ | H | H | OCH | CH | N | |

TABLE IVa

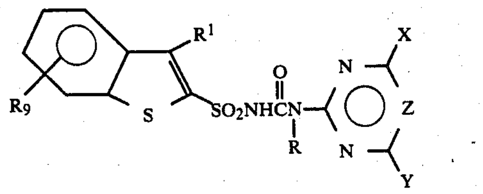

| $R^1$ | $R_9$ | R | X | Y | Z | m.p. (°C.) |
|---|---|---|---|---|---|---|
| H | H | H | $CH_3$ | $CH_3$ | CH | |
| H | H | H | $OCH_3$ | $OCH_3$ | CH | |
| H | H | H | $CH_3$ | $CH_3$ | N | |
| $CH_3$ | 7-Cl | H | $CH_3$ | $OCH_3$ | CH | |
| $CH_3$ | H | H | $CH_3$ | $CH_3$ | CH | |
| $CH_3$ | H | H | $OCH_3$ | $OCH_3$ | CH | |
| $CH(CH_3)_2$ | H | H | $OCH_3$ | $CH_3$ | CH | |
| $CH(CH_3)_2$ | H | H | $OCH_3$ | $CH_3$ | N | |
| $C_2H_5$ | H | H | $OCH_3$ | $OCH_3$ | CN | |
| $C_2H_5$ | 5-$NO_2$ | H | $CH_3$ | $OCH_3$ | N | |
| Cl | H | H | $CH_3$ | $OCH_3$ | N | |
| Cl | H | H | $CH_3$ | $CH_3$ | CH | |
| Cl | H | H | $CH_3$ | $CH_3$ | N | |
| Cl | H | H | $CH_3$ | $OCH_3$ | CH | |
| Cl | H | H | $OCH_3$ | $OCH_3$ | CH | |
| Cl | H | H | $OCH_3$ | $OCH_3$ | N | |
| Br | H | H | $OCH_3$ | $OCH_3$ | CH | |
| Br | 6-$CH_3$ | H | $OCH_3$ | $CH_3$ | N | |
| $OCH_3$ | H | H | $CH_3$ | $OCH_3$ | CH | |
| $OCH_3$ | H | H | $CH_3$ | $OCH_3$ | N | |
| $OC_2H_5$ | H | H | $OCH_3$ | $OCH_3$ | CH | |
| $O(CH_2)_3H$ | H | H | $OCH_3$ | $CH_3$ | CH | |
| $CO_2CH_3$ | H | H | $CH_3$ | $CH_3$ | CH | |
| $CO_2CH_3$ | H | H | $CH_3$ | $OCH_3$ | CH | |
| $CO_2CH_3$ | H | H | $OCH_3$ | $OCH_3$ | CH | |
| H | H | H | $CH_3$ | $OCH_3$ | CH | |
| H | H | H | $CH_3$ | $OCH_3$ | N | |
| H | H | H | $OCH_3$ | $OCH_3$ | N | |
| $CO_2CH_3$ | H | H | $CH_3$ | $CH_3$ | N | |
| $CO_2CH_3$ | H | H | $CH_3$ | $OCH_3$ | N | |
| $CO_2CH_3$ | H | H | $OCH_3$ | $OCH_3$ | N | |
| $CO_2CH_3$ | H | $CH_3$ | $OCH_3$ | $OCH_3$ | N | |
| $CO_2CH_3$ | H | H | $CH_3$ | $OCH_3$ | CCl | |
| $CO_2CH_3$ | H | H | $CH_3$ | $CH_3$ | CCl | |
| $CO_2CH_3$ | H | H | $CH_3$ | $OCH_3$ | CBr | |
| $CO_2CH_3$ | H | H | $CH_3$ | $NH_2$ | CH | |
| $CO_2CH_3$ | H | H | $CH_3$ | $NHCH_3$ | CH | |
| $CO_2CH_3$ | H | H | $CH_3$ | $N(CH_3)_2$ | CH | |
| $CO_2CH_3$ | H | H | $CH_3$ | $SCH_3$ | CH | |
| $CO_2CH_3$ | 4-Cl | H | $CH_3$ | $CH_3$ | CH | |
| $CO_2CH_3$ | 4-Cl | H | $CH_3$ | $OCH_3$ | CH | |
| $CO_2CH_3$ | 4-Cl | H | $OCH_3$ | $OCH_3$ | CH | |
| $CO_2CH_3$ | 4-Cl | H | $CH_3$ | $CH_3$ | N | |
| $CO_2CH_3$ | 4-Cl | H | $CH_3$ | $OCH_3$ | N | |
| $CO_2CH_3$ | 4-Cl | H | $OCH_3$ | $OCH_3$ | N | |
| $CO_2CH_3$ | 4-Cl | $CH_3$ | $OCH_3$ | $OCH_3$ | N | |
| $CO_2CH_3$ | 4-$NO_2$ | H | $CH_3$ | $CH_3$ | CH | |
| $CO_2CH_3$ | 4-$NO_2$ | H | $CH_3$ | $OCH_3$ | CH | |
| $CO_2CH_3$ | 4-$NO_2$ | H | $OCH_3$ | $OCH_3$ | CH | |
| $CO_2CH_3$ | 4-$NO_2$ | H | $CH_3$ | $CH_3$ | N | |
| $CO_2CH_3$ | 4-$NO_2$ | H | $CH_3$ | $OCH_3$ | N | |
| $CO_2CH_3$ | 4-$NO_2$ | H | $OCH_3$ | $OCH_3$ | N | |
| $CO_2CH_3$ | 4-$NO_2$ | $CH_3$ | $OCH_3$ | $OCH_3$ | N | |
| $CO_2CH_3$ | H | H | $CH_3$ | $OCH_3$ | CBr | |
| $CO_2CH_3$ | H | H | $CH_3$ | $OCH_3$ | CCN | |
| $CO_2CH_3$ | 7-$OCH_3$ | H | $CH_3$ | $OCH_3$ | CCN | |
| $CO_2CH_3$ | H | H | $CH_3$ | $OCH_{33}$ | $CCH_3$ | |
| $CO_2CH_3$ | H | H | $CH_3$ | $OCH_3$ | $CC_2H_5$ | |
| $CO_2CH_3$ | H | H | $OCH_3$ | $OCH_3$ | $CCH_2CH_3$ | |
| $CO_2CH_3$ | H | H | $OCH_3$ | $OCH_3$ | $CCH_3$ | |
| $CO_2CH_3$ | H | H | $CH_3$ | $OCH_3$ | $CCH_2CH_2Cl$ | |
| $CO_2CH_3$ | H | H | $OCH_3$ | $OCH_3$ | $CCH_2CH_2Cl$ | |
| $CO_2CH_3$ | H | H | $CH_3$ | $OCH_3$ | $CCH_2CH{=}CH_2$ | |
| $CO_2CH_3$ | 6-Br | H | $CH_3$ | $OCH_3$ | $CCH_2CH{=}CH_2$ | |
| $SO_2CH_3$ | H | H | $CH_3$ | $CH_3$ | CH | |
| $SO_2CH_3$ | H | H | $CH_3$ | $OCH_3$ | CH | |
| $SO_2CH_3$ | H | H | $OCH_3$ | $OCH_3$ | CH | |
| $SO_2CH_3$ | H | H | $CH_3$ | $CH_3$ | N | |
| $SO_2CH_3$ | H | H | $CH_3$ | $OCH_3$ | N | |
| $SO_2CH_3$ | H | H | $OCH_3$ | $OCH_3$ | N | |

TABLE IVa-continued

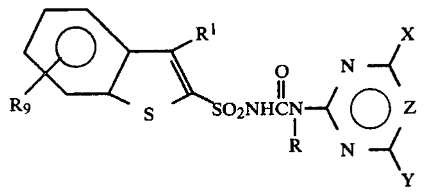

| $R^1$ | $R_9$ | R | X | Y | Z | m.p. (°C.) |
|---|---|---|---|---|---|---|
| $SO_2CH_3$ | H | $CH_3$ | $OCH_3$ | $OCH_3$ | N | |
| $SO_2C_2H_5$ | H | H | $CH_3$ | $CH_3$ | CH | |
| $SO_2C_2H_5$ | H | H | $CH_3$ | $OCH_3$ | CH | |
| $SO_2C_2H_5$ | H | H | $OCH_3$ | $OCH_3$ | CH | |
| $SO_2C_2H_5$ | H | H | $CH_3$ | $CH_3$ | N | |
| $SO_2C_2H_5$ | H | H | $CH_3$ | $OCH_3$ | N | |
| $SO_2C_2H_5$ | H | H | $OCH_3$ | $OCH_3$ | N | |
| $SO_2C_2H_5$ | H | $CH_3$ | $OCH_3$ | $OCH_3$ | N | |
| $SO_2CH(CH_3)_2$ | H | H | $CH_3$ | $CH_3$ | CH | |
| $SO_2(CH_2)_3H$ | H | H | OCH | CH | N | |
| $SO_2(CH_2)_4H$ | H | H | $OCH_3$ | $CH_3$ | N | |
| $SO_2N(CH_3)_2$ | H | H | $CH_3$ | $CH_3$ | CH | |
| $SO_2N(CH_3)_2$ | H | H | $CH_3$ | $OCH_3$ | CH | |
| $SO_2N(CH_3)_2$ | H | H | $OCH_3$ | $OCH_3$ | CH | |
| $SO_2N(CH_3)_2$ | H | H | $CH_3$ | $CH_3$ | N | |
| $SO_2N(CH_3)_2$ | H | H | $CH_3$ | $OCH_3$ | N | |
| $SO_2N(CH_3)_2$ | H | H | $OCH_3$ | $OCH_3$ | N | |
| $SO_2N(CH_3)_2$ | H | $CH_3$ | $OCH_3$ | $OCH_3$ | N | |
| $SO_2N(C_2H_5)_2$ | H | H | $OCH_3$ | $OCH_3$ | N | |
| $SO_2N(C_2H_5)_2$ | 5-$CH_3$ | H | $OCH_3$ | $OCH_3$ | CH | |
| $SO_2N(CH_3)C_2H_5$ | H | H | $CH_3$ | $OCH_3$ | CH | |
| $CO_2CH_3$ | H | H | H | $CH_3$ | N | |
| $CO_2CH_3$ | H | H | $OC_2H_5$ | $OC_2H_5$ | N | |
| $CO_2CH_3$ | H | H | $OC_2H_5$ | $OC_2H_5$ | CH | |
| $CO_2CH_3$ | H | H | $OCH_2CF_3$ | $OCH_3$ | CH | |
| $CO_2CH_3$ | H | H | $CH_2OCH_3$ | $OCH_3$ | N | |
| $CO_2CH_3$ | H | H | $CH_2OCH_3$ | $CH_3$ | N | |
| $CO_2CH_3$ | H | $CH_3$ | $OCH_3$ | $OCH_3$ | CH | |
| $CO_2CH_3$ | H | H | Cl | Cl | N | |
| $CO_2C_2H_5$ | H | H | $CH_3$ | $CH_3$ | CH | |
| $CO_2C_2H_5$ | H | H | $CH_3$ | $OCH_3$ | CH | |
| $CO_2C_2H_5$ | H | H | $OCH_3$ | $OCH_3$ | CH | |
| $CO_2C_2H_5$ | H | H | $CH_3$ | $CH_3$ | N | |
| $CO_2C_2H_5$ | H | H | $CH_3$ | $OCH_3$ | N | |
| $CO_2C_2H_5$ | H | H | $OCH_3$ | $OCH_3$ | N | |
| $CO_2C_2H_5$ | H | $CH_3$ | $OCH_3$ | $OCH_3$ | N | |
| $CO_2(CH_2)_3H$ | H | H | $OCH_3$ | $OCH_3$ | CH | |
| $CO_2(CH_2)_3H$ | H | H | $CH_3$ | $OCH_3$ | N | |
| $CON(CH_3)_2$ | H | H | $CH_3$ | $OCH_3$ | N | |
| $CON(CH_3)_2$ | H | H | $CH_3$ | $CH_3$ | CH | |
| $CON(CH_3)_2$ | H | H | $OCH_3$ | $OCH_3$ | CH | |
| $CON(CH_3)_2$ | H | H | $CH_3$ | $OCH_3$ | CH | |
| $CON(CH_3)_2$ | H | H | $CH_3$ | $CH_3$ | N | |
| $CON(CH_3)_2$ | H | H | $OCH_3$ | $OCH_3$ | N | |
| $CON(CH_3)_2$ | H | $CH_3$ | $OCH_3$ | $OCH_3$ | N | |
| $CON(C_2H_5)_2$ | 7-Cl | H | $OCH_3$ | $CH_3$ | N | |
| $CON(CH_3)CH(CH_3)$ | H | H | $CH_3$ | $CH_3$ | CH | |
| 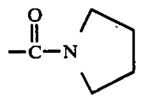 | H | H | $OCH_3$ | $CH_3$ | N | |
| $SO_2N(CH_3)CH(CH_3)_2$ | H | H | $CH_3$ | $CH_3$ | CH | |
| $SO_2(CH_3) (CH_2)_3H$ | H | H | $OCH_3$ | $OCH_3$ | CH | |
| $CO_2CH_3$ | H | H | $CH_3$ | Cl | N | |
| $CO_2CH_3$ | H | H | $OCH_3$ | Cl | N | |
| $CO_2CH_3$ | H | H | $OCH_2CF_3$ | Cl | N | |
| $SO_2N(CH_3)OCH_3$ | H | H | $CH_3$ | $CH_3$ | CH | |
| $SO_2N(CH_3)OCH_3$ | H | H | $CH_3$ | $OCH_3$ | CH | |
| $SO_2N(CH_3)OCH_3$ | H | H | $OCH_3$ | $OCH_3$ | CH | |
| $SO_2N(CH_3)OCH_3$ | H | H | $CH_3$ | $CH_3$ | N | |
| $SO_2N(CH_3)OCH_3$ | H | H | $CH_3$ | $OCH_3$ | N | |
| $SO_2N(CH_3)OCH_3$ | H | H | $OCH_3$ | $OCH_3$ | N | |
| $SO_2N(CH_3)OCH_3$ | H | $CH_3$ | $OCH_3$ | $OCH_3$ | N | |

TABLE IVb

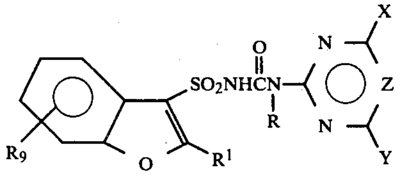

| $R^1$ | $R_9$ | R | X | Y | Z | m.p. (°C.) |
|---|---|---|---|---|---|---|
| H | H | H | X | $CH_3$ | CH | |
| H | H | H | $OCH_3$ | $OCH_3$ | CH | |
| H | H | H | $CH_3$ | $CH_3$ | N | |
| $CH_3$ | 7-Cl | H | $CH_3$ | $OCH_3$ | CH | |
| $CH_3$ | H | H | $CH_3$ | $CH_3$ | CH | |
| $CH_3$ | H | H | $OCH_3$ | $OCH_3$ | CH | |
| $CH(CH_3)_2$ | H | H | $OCH_3$ | $CH_3$ | CH | |
| $CH(CH_3)_2$ | H | H | $OCH_3$ | $CH_3$ | N | |
| $C_2H_5$ | H | H | $OCH_3$ | $OCH_3$ | CN | |
| $C_2H_5$ | 5-$NO_2$ | H | $CH_3$ | $OCH_3$ | N | |
| Cl | H | H | $CH_3$ | $OCH_3$ | N | |
| Cl | H | H | $CH_3$ | $CH_3$ | CH | |
| Cl | H | H | $CH_3$ | $CH_3$ | N | |
| Cl | H | H | $CH_3$ | $OCH_3$ | CH | |
| Cl | H | H | $OCH_3$ | $OCH_3$ | CH | |
| Cl | H | H | $OCH_3$ | $OCH_3$ | N | |
| Br | H | H | $OCH_3$ | $OCH_3$ | CH | |
| Br | 6-$CH_3$ | H | $OCH_3$ | $CH_3$ | N | |
| $OCH_3$ | H | H | $CH_3$ | $OCH_3$ | CH | |
| $OCH_3$ | H | H | $CH_3$ | $OCH_3$ | N | |
| $OC_2H_5$ | H | H | $OCH_3$ | $OCH_3$ | CH | |
| $O(CH_2)_3H$ | H | H | $OCH_3$ | $CH_3$ | CH | |
| $CO_2CH_3$ | H | H | $CH_3$ | $CH_3$ | CH | |
| $CO_2CH_3$ | H | H | $CH_3$ | $OCH_3$ | CH | |
| $CO_2CH_3$ | H | H | $OCH_3$ | $OCH_3$ | CH | |
| H | H | H | $CH_3$ | $OCH_3$ | CH | |
| H | H | H | $CH_3$ | $OCH_3$ | N | |
| H | H | H | $OCH_3$ | $OCH_3$ | N | |
| $CO_2CH_3$ | H | H | $CH_3$ | $CH_3$ | N | |
| $CO_2CH_3$ | H | H | $CH_3$ | $OCH_3$ | N | |
| $CO_2CH_3$ | H | H | $OCH_3$ | $OCH_3$ | N | |
| $CO_2CH_3$ | H | $CH_3$ | $OCH_3$ | $OCH_3$ | N | |
| $CO_2CH_3$ | H | H | $CH_3$ | $OCH_3$ | CCl | |
| $CO_2CH_3$ | H | H | $CH_3$ | $CH_3$ | CCl | |
| $CO_2CH_3$ | H | H | $CH_3$ | $OCH_3$ | CBr | |
| $CO_2CH_3$ | H | H | $CH_3$ | $NH_2$ | CH | |
| $CO_2CH_3$ | H | H | $CH_3$ | $NHCH_3$ | CH | |
| $CO_2CH_3$ | H | H | $CH_3$ | $N(CH_3)_2$ | CH | |
| $CO_2CH_3$ | H | H | $CH_3$ | $SCH_3$ | CH | |
| $CO_2CH_3$ | 4-Cl | H | $CH_3$ | $CH_3$ | CH | |
| $CO_2CH_3$ | 4-Cl | H | $CH_3$ | $OCH_3$ | CH | |
| $CO_2CH_3$ | 4-Cl | H | $OCH_3$ | $OCH_3$ | CH | |
| $CO_2CH_3$ | 4-Cl | H | $CH_3$ | $CH_3$ | N | |
| $CO_2CH_3$ | 4-Cl | H | $CH_3$ | $OCH_3$ | N | |
| $CO_2CH_3$ | 4-Cl | H | $OCH_3$ | $OCH_3$ | N | |
| $CO_2CH_3$ | 4-Cl | $CH_3$ | $OCH_3$ | $OCH_3$ | N | |
| $CO_2CH_3$ | 4-$NO_2$ | H | $CH_3$ | $CH_3$ | CH | |
| $CO_2CH_3$ | 4-$NO_2$ | H | $CH_3$ | $OCH_3$ | CH | |
| $CO_2CH_3$ | 4-$NO_2$ | H | $OCH_3$ | $OCH_3$ | CH | |
| $CO_2CH_3$ | 4-$NO_2$ | H | $CH_3$ | $CH_3$ | N | |
| $CO_2CH_3$ | 4-$NO_2$ | H | $CH_3$ | $OCH_3$ | N | |
| $CO_2CH_3$ | 4-$NO_2$ | H | $OCH_3$ | $OCH_3$ | N | |
| $CO_2CH_3$ | 4-$NO_2$ | $CH_3$ | $OCH_3$ | $OCH_3$ | N | |
| $CO_2CH_3$ | H | H | $CH_3$ | $OCH_3$ | CBr | |
| $CO_2CH_3$ | H | H | $CH_3$ | $OCH_3$ | CCN | |
| $CO_2CH_3$ | 7-$OCH_3$ | H | $CH_3$ | $OCH_3$ | CCN | |
| $CO_2CH_3$ | H | H | $CH_3$ | $OCH_3$ | $CCH_3$ | |
| $CO_2CH_3$ | H | H | $CH_3$ | $OCH_3$ | $CC_2H_5$ | |
| $CO_2CH_3$ | H | H | $OCH_3$ | $OCH_3$ | $CCH_2CH_3$ | |
| $CO_2CH_3$ | H | H | $OCH_3$ | $OCH_3$ | $CCH_3$ | |
| $CO_2CH_3$ | H | H | $CH_3$ | $OCH_3$ | $CCH_2CH_2Cl$ | |
| $CO_2CH_3$ | H | H | $OCH_3$ | $OCH_3$ | $CCH_2CH_2Cl$ | |
| $CO_2CH_3$ | H | H | $CH_3$ | $OCH_3$ | $CCH_2CH{=}CH_2$ | |
| $CO_2CH_3$ | 6-Br | H | $CH_3$ | $OCH_3$ | $CCH_2CH{=}CH_2$ | |
| $SO_2CH_3$ | H | H | $CH_3$ | $CH_3$ | CH | |
| $SO_2CH_3$ | H | H | $CH_3$ | $OCH_3$ | CH | |
| $SO_2CH_3$ | H | H | $OCH_3$ | $OCH_3$ | CH | |
| $SO_2CH_3$ | H | H | $CH_3$ | $CH_3$ | N | |
| $SO_2CH_3$ | H | H | $CH_3$ | $OCH_3$ | N | |
| $SO_2CH_3$ | H | H | $OCH_3$ | $OCH_3$ | N | |
| $SO_2CH_3$ | H | $CH_3$ | $OCH_3$ | $OCH_3$ | N | |

TABLE IVb-continued

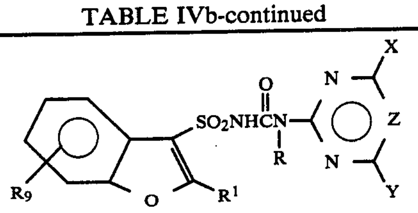

| $R^1$ | $R_9$ | R | X | Y | Z | m.p. (°C.) |
|---|---|---|---|---|---|---|
| $SO_2C_2H_5$ | H | H | $CH_3$ | $CH_3$ | CH | |
| $SO_2C_2H_5$ | H | H | $CH_3$ | $OCH_3$ | CH | |
| $SO_2C_2H_5$ | H | H | $OCH_3$ | $OCH_3$ | CH | |
| $SO_2C_2H_5$ | H | H | $CH_3$ | $CH_3$ | N | |
| $SO_2C_2H_5$ | H | H | $CH_3$ | $OCH_3$ | N | |
| $SO_2C_2H_5$ | H | H | $OCH_3$ | $OCH_3$ | N | |
| $SO_2C_2H_5$ | H | $CH_3$ | $OCH_3$ | $OCH_3$ | N | |
| $SO_2CH(CH_3)_2$ | H | H | $CH_3$ | $CH_3$ | CH | |
| $SO_2(CH_2)_3H$ | H | H | OCH | CH | N | |
| $SO_2(CH_2)_4H$ | H | H | $OCH_3$ | $CH_3$ | N | |
| $SO_2N(CH_3)_2$ | H | H | $CH_3$ | $CH_3$ | CH | |
| $SO_2N(CH_3)_2$ | H | H | $CH_3$ | $OCH_3$ | CH | |
| $SO_2N(CH_3)_2$ | H | H | $OCH_3$ | $OCH_3$ | CH | |
| $SO_2N(CH_3)_2$ | H | H | $CH_3$ | $CH_3$ | N | |
| $SO_2N(CH_3)_2$ | H | H | $CH_3$ | $OCH_3$ | N | |
| $SO_2N(CH_3)_2$ | H | H | $OCH_3$ | $OCH_3$ | N | |
| $SO_2N(CH_3)_2$ | H | $CH_3$ | $OCH_3$ | $OCH_3$ | N | |
| $SO_2N(C_2H_5)_2$ | H | H | $OCH_3$ | $OCH_3$ | N | |
| $SO_2N(C_2H_5)_2$ | 5-$CH_3$ | H | $OCH_3$ | $OCH_3$ | CH | |
| $SO_2N(CH_3)C_2H_5$ | H | H | $CH_3$ | $OCH_3$ | CH | |
| $CO_2CH_3$ | H | H | H | $CH_3$ | N | |
| $CO_2CH_3$ | H | H | $OC_2H_5$ | $OC_2H_5$ | N | |
| $CO_2CH_3$ | H | H | $OC_2H_5$ | $OC_2H_5$ | CH | |
| $CO_2CH_3$ | H | H | $OCH_2CF_3$ | $OCH_3$ | CH | |
| $CO_2CH_3$ | H | H | $CH_2OCH_3$ | $OCH_3$ | N | |
| $CO_2CH_3$ | H | H | $CH_2OCH_3$ | $CH_3$ | N | |
| $CO_2CH_3$ | H | $CH_3$ | $OCH_3$ | $OCH_3$ | CH | |
| $CO_2CH_3$ | H | H | Cl | Cl | N | |
| $CO_2C_2H_5$ | H | H | $CH_3$ | $CH_3$ | CH | |
| $CO_2C_2H_5$ | H | H | $CH_3$ | $OCH_3$ | CH | |
| $CO_2C_2H_5$ | H | H | $OCH_3$ | $OCH_3$ | CH | |
| $CO_2C_2H_5$ | H | H | $CH_3$ | $CH_3$ | N | |
| $CO_2C_2H_5$ | H | H | $CH_3$ | $OCH_3$ | N | |
| $CO_2C_2H_5$ | H | H | $OCH_3$ | $OCH_3$ | N | |
| $CO_2C_2H_5$ | H | $CH_3$ | $OCH_3$ | $OCH_3$ | N | |
| $CO_2(CH_2)_3H$ | H | H | $OCH_3$ | $OCH_3$ | CH | |
| $CO_2(CH_2)_3H$ | H | H | $CH_3$ | $OCH_3$ | N | |
| $CON(CH_3)_2$ | H | H | $CH_3$ | $OCH_3$ | N | |
| $CON(CH_3)_2$ | H | H | $CH_3$ | $CH_3$ | CH | |
| $CON(CH_3)_2$ | H | H | $OCH_3$ | $OCH_3$ | CH | |
| $CON(CH_3)_2$ | H | H | $CH_3$ | $OCH_3$ | CH | |
| $CON(CH_3)_2$ | H | H | $CH_3$ | $CH_3$ | N | |
| $CON(CH_3)_2$ | H | H | $OCH_3$ | $OCH_3$ | N | |
| $CON(CH_3)_2$ | H | $CH_3$ | $OCH_3$ | $OCH_3$ | N | |
| $CON(C_2H_5)_2$ | 7-Cl | H | $OCH_3$ | $CH_3$ | N | |
| $CON(CH_3)CH(CH_3)_2$ | H | H | $CH_3$ | $CH_3$ | CH | |
| 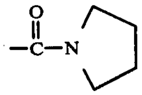 | H | H | $OCH_3$ | $CH_3$ | N | |
| $SO_2N(CH_3)CH(CH_3)_2$ | H | H | $CH_3$ | $CH_3$ | CH | |
| $SO_2N(CH_3)$ $(CH_2)_3H$ | H | H | $OCH_3$ | $OCH_3$ | CH | |
| $CO_2CH_3$ | H | H | $CH_3$ | Cl | N | |
| $CO_2CH_3$ | H | H | $OCH_3$ | Cl | N | |
| $CO_2CH_3$ | H | H | $OCH_2CF_3$ | Cl | N | |
| $SO_2N(CH_3)OCH_3$ | H | H | $CH_3$ | $CH_3$ | CH | |
| $SO_2N(CH_3)OCH_3$ | H | H | $CH_3$ | $OCH_3$ | CH | |
| $SO_2N(CH_3)OCH_3$ | H | H | $OCH_3$ | $OCH_3$ | CH | |
| $SO_2N(CH_3)OCH_3$ | H | H | $CH_3$ | $CH_3$ | N | |
| $SO_2N(CH_3)OCH_3$ | H | H | $CH_3$ | $OCH_3$ | N | |
| $SO_2N(CH_3)OCH_3$ | H | H | $OCH_3$ | $OCH_3$ | N | |
| $SO_2N(CH_3)OCH_3$ | H | $CH_3$ | $OCH_3$ | $OCH_3$ | N | |

TABLE IVc

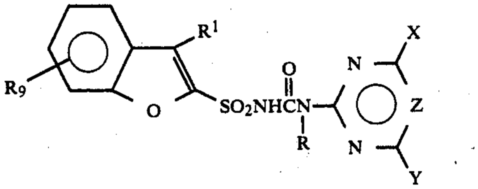

| $R^1$ | $R_9$ | R | X | Y | Z | m.p. (°C.) |
|---|---|---|---|---|---|---|
| H | H | H | $CH_3$ | $CH_3$ | CH | |
| H | H | H | $OCH_3$ | $OCH_3$ | CH | |
| H | H | H | $CH_3$ | $CH_3$ | N | |
| $CH_3$ | 7-Cl | H | $CH_3$ | $OCH_3$ | CH | |
| $CH_3$ | H | H | $CH_3$ | $CH_3$ | CH | |
| $CH_3$ | H | H | $OCH_3$ | $OCH_3$ | CH | |
| $CH(CH_3)_2$ | H | H | $OCH_3$ | $CH_3$ | CH | |
| $CH(CH_3)_2$ | H | H | $OCH_3$ | $CH_3$ | N | |
| $C_2H_5$ | H | H | $OCH_3$ | $OCH_3$ | CN | |
| $C_2H_5$ | 5-$NO_2$ | H | $CH_3$ | $OCH_3$ | N | |
| Cl | H | H | $CH_3$ | $OCH_3$ | N | |
| Cl | H | H | $CH_3$ | $CH_3$ | CH | |
| Cl | H | H | $CH_3$ | $CH_3$ | N | |
| Cl | H | H | $CH_3$ | $OCH_3$ | CH | |
| Cl | H | H | $OCH_3$ | $OCH_3$ | CH | |
| Cl | H | H | $OCH_3$ | $OCH_3$ | N | |
| Br | H | H | $OCH_3$ | $OCH_3$ | CH | |
| Br | 6-$CH_3$ | H | $OCH_3$ | $CH_3$ | N | |
| $OCH_3$ | H | H | $CH_3$ | $OCH_3$ | CH | |
| $OCH_3$ | H | H | $CH_3$ | $OCH_3$ | N | |
| $OC_2H_5$ | H | H | $OCH_3$ | $OCH_3$ | CH | |
| $O(CH_2)_3H$ | H | H | $OCH_3$ | $CH_3$ | CH | |
| $CO_2CH_3$ | H | H | $CH_3$ | $CH_3$ | CH | |
| $CO_2CH_3$ | H | H | $CH_3$ | $OCH_3$ | CH | |
| $CO_2CH_3$ | H | H | $OCH_3$ | $OCH_3$ | CH | |
| H | H | H | $CH_3$ | $OCH_3$ | CH | |
| H | H | H | $CH_3$ | $OCH_3$ | N | |
| H | H | H | $OCH_3$ | $OCH_3$ | N | |
| $CO_2CH_3$ | H | H | $CH_3$ | $CH_3$ | N | |
| $CO_2CH_3$ | H | H | $CH_3$ | $OCH_3$ | N | |
| $CO_2CH_3$ | H | H | $OCH_3$ | $OCH_3$ | N | |
| $CO_2CH_3$ | H | $CH_3$ | $OCH_3$ | $OCH_3$ | N | |
| $CO_2CH_3$ | H | H | $CH_3$ | $OCH_3$ | CCl | |
| $CO_2CH_3$ | H | H | $CH_3$ | $CH_3$ | CCl | |
| $CO_2CH_3$ | H | H | $CH_3$ | $OCH_3$ | CBr | |
| $CO_2CH_3$ | H | H | $CH_3$ | $NH_2$ | CH | |
| $CO_2CH_3$ | H | H | $CH_3$ | $NHCH_3$ | CH | |
| $CO_2CH_3$ | H | H | $CH_3$ | $N(CH_3)_2$ | CH | |
| $CO_2CH_3$ | H | H | $CH_3$ | $SCH_3$ | CH | |
| $CO_2CH_3$ | 4-Cl | H | $CH_3$ | $CH_3$ | CH | |
| $CO_2CH_3$ | 4-Cl | H | $CH_3$ | $OCH_3$ | CH | |
| $CO_2CH_3$ | 4-Cl | H | $OCH_3$ | $OCH_3$ | CH | |
| $CO_2CH_3$ | 4-Cl | H | $CH_3$ | $CH_3$ | N | |
| $CO_2CH_3$ | 4-Cl | H | $CH_3$ | $OCH_3$ | N | |
| $CO_2CH_3$ | 4-Cl | H | $OCH_3$ | $OCH_3$ | N | |
| $CO_2CH_3$ | 4-Cl | $CH_3$ | $OCH_3$ | $OCH_3$ | N | |
| $CO_2CH_3$ | 4-$NO_2$ | H | $CH_3$ | $CH_3$ | CH | |
| $CO_2CH_3$ | 4-$NO_2$ | H | $CH_3$ | $OCH_3$ | CH | |
| $CO_2CH_3$ | 4-$NO_2$ | H | $OCH_3$ | $OCH_3$ | CH | |
| $CO_2CH_3$ | 4-$NO_2$ | H | $CH_3$ | $CH_3$ | N | |
| $CO_2CH_3$ | 4-$NO_2$ | H | $CH_3$ | $OCH_3$ | N | |
| $CO_2CH_3$ | 4-$NO_2$ | H | $OCH_3$ | $OCH_3$ | N | |
| $CO_2CH_3$ | 4-$NO_2$ | $CH_3$ | $OCH_3$ | $OCH_3$ | N | |
| $CO_2CH_3$ | H | H | $CH_3$ | $OCH_3$ | CBr | |
| $CO_2CH_3$ | H | H | $CH_3$ | $OCH_3$ | CCN | |
| $CO_2CH_3$ | 7-$OCH_3$ | H | $CH_3$ | $OCH_3$ | CCN | |
| $CO_2CH_3$ | H | H | $CH_3$ | $OCH_3$ | $CCH_3$ | |
| $CO_2CH_3$ | H | H | $CH_3$ | $OCH_3$ | $CC_2H_5$ | |
| $CO_2CH_3$ | H | H | $OCH_3$ | $OCH_3$ | $CCH_2CH_3$ | |
| $CO_2CH_3$ | H | H | $OCH_3$ | $OCH_3$ | $CCH_3$ | |
| $CO_2CH_3$ | H | H | $CH_3$ | $OCH_3$ | $CCH_2CH_2Cl$ | |
| $CO_2CH_3$ | H | H | $OCH_3$ | $OCH_3$ | $CCH_2CH_2Cl$ | |
| $CO_2CH_3$ | H | H | $CH_3$ | $OCH_3$ | $CCH_2CH{=}CH_2$ | |
| $CO_2CH_3$ | 6-Br | H | $CH_3$ | $OCH_3$ | $CCH_2CH{=}CH_2$ | |
| $SO_2CH_3$ | H | H | $CH_3$ | $CH_3$ | CH | |
| $SO_2CH_3$ | H | H | $CH_3$ | $OCH_3$ | CH | |
| $SO_2CH_3$ | H | H | $OCH_3$ | $OCH_3$ | CH | |
| $SO_2CH_3$ | H | H | $CH_3$ | $CH_3$ | N | |
| $SO_2CH_3$ | H | H | $CH_3$ | $OCH_3$ | N | |
| $SO_2CH_3$ | H | H | $OCH_3$ | $OCH_3$ | N | |

TABLE IVc-continued

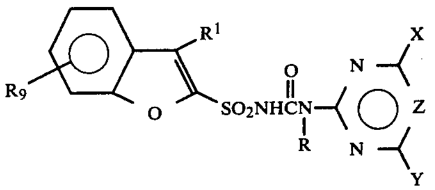

| $R^1$ | $R_9$ | R | X | Y | Z | m.p. (°C.) |
|---|---|---|---|---|---|---|
| $SO_2CH_3$ | H | $CH_3$ | $OCH_3$ | $OCH_3$ | N | |
| $SO_2C_2H_5$ | H | H | $CH_3$ | $CH_3$ | CH | |
| $SO_2C_2H_5$ | H | H | $CH_3$ | $OCH_3$ | CH | |
| $SO_2C_2H_5$ | H | H | $OCH_3$ | $OCH_3$ | CH | |
| $SO_2C_2H_5$ | H | H | $CH_3$ | $CH_3$ | N | |
| $SO_2C_2H_5$ | H | H | $CH_3$ | $OCH_3$ | N | |
| $SO_2C_2H_5$ | H | H | $OCH_3$ | $OCH_3$ | N | |
| $SO_2C_2H_5$ | H | $CH_3$ | $OCH_3$ | $OCH_3$ | N | |
| $SO_2CH(CH_3)_2$ | H | H | $CH_3$ | $CH_3$ | CH | |
| $SO_2(CH_2)_3H$ | H | H | OCH | CH | N | |
| $SO_2(CH_2)_4H$ | H | H | $OCH_3$ | $CH_3$ | N | |
| $SO_2N(CH_3)_2$ | H | H | $CH_3$ | $CH_3$ | CH | |
| $SO_2N(CH_3)_2$ | H | H | $CH_3$ | $OCH_3$ | CH | |
| $SO_2N(CH_3)_2$ | H | H | $OCH_3$ | $OCH_3$ | CH | |
| $SO_2N(CH_3)_2$ | H | H | $CH_3$ | $CH_3$ | N | |
| $SO_2N(CH_3)_2$ | H | H | $CH_3$ | $OCH_3$ | N | |
| $SO_2N(CH_3)_2$ | H | H | $OCH_3$ | $OCH_3$ | N | |
| $SO_2N(CH_3)_2$ | H | $CH_3$ | $OCH_3$ | $OCH_3$ | N | |
| $SO_2N(C_2H_5)_2$ | H | H | $OCH_3$ | $OCH_3$ | N | |
| $SO_2N(C_2H_5)_2$ | 5-$CH_3$ | H | $OCH_3$ | $OCH_3$ | CH | |
| $SO_2N(CH_3)C_2H_5$ | H | H | $CH_3$ | $OCH_3$ | CH | |
| $CO_2CH_3$ | H | H | H | $CH_3$ | N | |
| $CO_2CH_3$ | H | H | $OC_2H_5$ | $OC_2H_5$ | N | |
| $CO_2CH_3$ | H | H | $OC_2H_5$ | $OC_2H_5$ | CH | |
| $CO_2CH_3$ | H | H | $OCH_2CF_3$ | $OCH_3$ | CH | |
| $CO_2CH_3$ | H | H | $CH_2OCH_3$ | $OCH_3$ | N | |
| $CO_2CH_3$ | H | H | $CH_2OCH_3$ | $CH_3$ | N | |
| $CO_2CH_3$ | H | $CH_3$ | $OCH_3$ | $OCH_3$ | CH | |
| $CO_2CH_3$ | H | H | Cl | Cl | N | |
| $CO_2C_2H_5$ | H | H | $CH_3$ | $CH_3$ | CH | |
| $CO_2C_2H_5$ | H | H | $CH_3$ | $OCH_3$ | CH | |
| $CO_2C_2H_5$ | H | H | $OCH_3$ | $OCH_3$ | CH | |
| $CO_2C_2H_5$ | H | H | $CH_3$ | $CH_3$ | N | |
| $CO_2C_2H_5$ | H | H | $CH_3$ | $OCH_3$ | N | |
| $CO_2C_2H_5$ | H | H | $OCH_3$ | $OCH_3$ | N | |
| $CO_2C_2H_5$ | H | $CH_3$ | $OCH_3$ | $OCH_3$ | N | |
| $CO_2(CH_2)_3H$ | H | H | $OCH_3$ | $OCH_3$ | CH | |
| $CO_2(CH_2)_3H$ | H | H | $CH_3$ | $OCH_3$ | N | |
| $CON(CH_3)_2$ | H | H | $CH_3$ | $OCH_3$ | N | |
| $CON(CH_3)_2$ | H | H | $CH_3$ | $CH_3$ | CH | |
| $CON(CH_3)_2$ | H | H | $OCH_3$ | $OCH_3$ | CH | |
| $CON(CH_3)_2$ | H | H | $CH_3$ | $OCH_3$ | CH | |
| $CON(CH_3)_2$ | H | H | $CH_3$ | $CH_3$ | N | |
| $CON(CH_3)_2$ | H | H | $OCH_3$ | $OCH_3$ | N | |
| $CON(CH_3)_2$ | H | $CH_3$ | $OCH_3$ | $OCH_3$ | N | |
| $CON(C_2H_5)_2$ | 7-Cl | H | $OCH_3$ | $CH_3$ | N | |
| $CON(CH_3)CH(CH_3)_2$ | H | H | $CH_3$ | $CH_3$ | CH | |
| 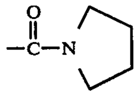 | H | H | $OCH_3$ | $CH_3$ | N | |
| $SO_2N(CH_3)CH(CH_3)_2$ | H | H | $CH_3$ | $CH_3$ | CH | |
| $SO_2N(CH_3)(CH_2)_3H$ | H | H | $OCH_3$ | $OCH_3$ | CH | |
| $CO_2CH_3$ | H | H | $CH_3$ | Cl | N | |
| $CO_2CH_3$ | H | H | $OCH_3$ | Cl | N | |
| $CO_2CH_3$ | H | H | $OCH_2CF_3$ | Cl | N | |
| $SO_2N(CH_3)OCH_3$ | H | H | $CH_3$ | $CH_3$ | CH | |
| $SO_2N(CH_3)OCH_3$ | H | H | $CH_3$ | $OCH_3$ | CH | |
| $SO_2N(CH_3)OCH_3$ | H | H | $OCH_3$ | $OCH_3$ | CH | |
| $SO_2N(CH_3)OCH_3$ | H | H | $CH_3$ | $CH_3$ | N | |
| $SO_2N(CH_3)OCH_3$ | H | H | $CH_3$ | $OCH_3$ | N | |
| $SO_2N(CH_3)OCH_3$ | H | H | $OCH_3$ | $OCH_3$ | N | |
| $SO_2N(CH_3)OCH_3$ | H | $CH_3$ | $OCH_3$ | $OCH_3$ | N | |

TABLE V

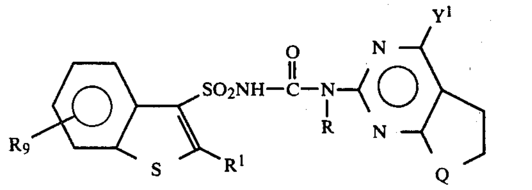

| $R^1$ | R | $R_9$ | $Y^1$ | Q | m.p. (°C.) |
|---|---|---|---|---|---|
| $CO_2CH_3$ | H | H | H | O | |
| $SO_2N(CH_3)_2$ | H | H | $CH_3$ | O | |
| Cl | H | H | H | O | |
| Br | H | H | H | O | |
| $NO_2$ | H | H | $CH_3$ | O | |
| H | H | H | $CH_3$ | O | |
| $CO_2CH_3$ | H | H | $CH_3$ | O | |
| $CO_2CH_3$ | H | H | $OCH_3$ | O | |
| $CO_2CH_3$ | H | H | Cl | O | |
| $CH_3$ | H | 6-$CH_3$ | $OCH_3$ | O | |
| $CH_2CH_3$ | H | H | $CH_3$ | O | |
| $CO_2CH(CH_3)_2$ | H | H | $CH_3$ | O | |
| $CO_2CH_3$ | $CH_3$ | H | $CH_3$ | O | 211-213° |
| $CO_2CH_3$ | $CH_3$ | H | $CH_3$ | $CH_2$ | |
| $CO_2CH_3$ | H | H | $OCH_3$ | $CH_2$ | |
| $CO_2CH(CH_3)_2$ | H | 7-$OCH_3$ | $OCH_3$ | $CH_2$ | |
| Cl | H | H | $OCH_3$ | $CH_2$ | |
| $NO_2$ | H | H | $OCH_3$ | $CH_2$ | |
| H | H | H | $OCH_3$ | $CH_2$ | |
| $CH_3$ | H | H | $OCH_3$ | $CH_2$ | |
| $C_2H_5$ | H | H | $OCH_3$ | $CH_2$ | |
| $CH(CH_3)_2$ | H | 5-$NO_2$ | H | $CH_2$ | |
| $CO_2CH_3$ | H | H | H | $CH_2$ | |
| $CO_2CH_3$ | H | H | $OCH_3$ | $CH_2$ | |
| $CO_2CH_3$ | H | 4-$NO_2$ | $CH_3$ | O | |
| $CO_2CH_3$ | H | 4-Cl | $CH_3$ | O | |

TABLE Va

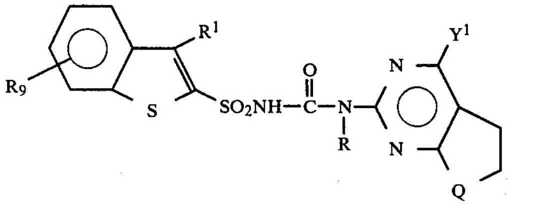

| $R^1$ | R | $R_9$ | $Y^1$ | Q |
|---|---|---|---|---|
| $CO_2CH_3$ | H | H | H | O |
| $SO_2N(CH_3)_2$ | H | H | $CH_3$ | O |
| Cl | H | H | H | O |
| Br | H | 6-$CH_3$ | H | O |
| $NO_2$ | H | H | $CH_3$ | O |
| H | H | H | $CH_3$ | O |
| $CO_2CH_3$ | H | H | $CH_3$ | O |
| $CO_2CH_3$ | H | H | $OCH_3$ | O |
| $CO_2CH_3$ | H | H | Cl | O |
| $CH_3$ | H | 4-Cl | $OCH_3$ | O |
| $CH_2CH_3$ | H | H | $CH_3$ | O |
| $CO_2CH(CH_3)_2$ | H | H | $CH_3$ | O |
| $CO_2CH_3$ | $CH_3$ | H | $CH_3$ | O |
| $CO_2CH_3$ | $CH_3$ | H | $CH_3$ | $CH_2$ |
| $CO_2CH_3$ | H | H | $OCH_3$ | $CH_2$ |
| $CO_2CH(CH_3)_2$ | H | 7-$OCH_3$ | $OCH_3$ | $CH_2$ |
| Cl | H | H | $OCH_3$ | $CH_2$ |
| $NO_2$ | H | H | $OCH_3$ | $CH_2$ |
| H | H | H | $OCH_3$ | $CH_2$ |
| $CH_3$ | H | H | $OCH_3$ | $CH_2$ |
| $C_2H_5$ | H | H | $OCH_3$ | $CH_2$ |
| $CH(CH_3)_2$ | H | 5-$NO_2$ | H | $CH_2$ |
| $CO_2CH_3$ | H | H | H | $CH_2$ |
| $CO_2CH_3$ | H | H | $OCH_3$ | $CH_2$ |
| $CO_2CH_3$ | H | 4-$NO_2$ | $CH_3$ | O |

TABLE Vb

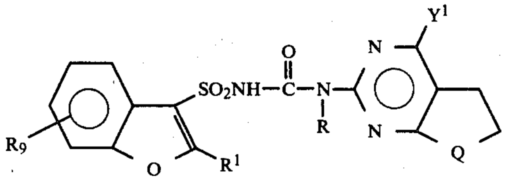

| $R^1$ | R | $R_9$ | $Y^1$ | Q |
|---|---|---|---|---|
| $CO_2CH_3$ | H | H | H | O |
| $SO_2N(CH_3)_2$ | H | H | $CH_3$ | O |
| Cl | H | H | H | O |
| Br | H | 6-$CH_3$ | H | O |
| $NO_2$ | H | H | $CH_3$ | O |
| H | H | H | $CH_3$ | O |
| $CO_2CH_3$ | H | H | $CH_3$ | O |
| $CO_2CH_3$ | H | H | $OCH_3$ | O |
| $CO_2CH_3$ | H | H | Cl | O |
| $CH_3$ | H | 4-Cl | $OCH_3$ | O |
| $CH_2CH_3$ | H | H | $CH_3$ | O |
| $CO_2CH(CH_3)_2$ | H | H | $CH_3$ | O |
| $CO_2CH_3$ | $CH_3$ | H | $CH_3$ | O |
| $CO_2CH_3$ | $CH_3$ | H | $CH_3$ | $CH_2$ |
| $CO_2CH_3$ | H | H | $OCH_3$ | $CH_2$ |
| $CO_2CH(CH_3)_2$ | H | 7-$OCH_3$ | $OCH_3$ | $CH_2$ |
| Cl | H | H | $OCH_3$ | $CH_2$ |
| $NO_2$ | H | H | $OCH_3$ | $CH_2$ |
| H | H | H | $OCH_3$ | $CH_2$ |
| $CH_3$ | H | H | $OCH_3$ | $CH_2$ |
| $C_2H_5$ | H | H | $OCH_3$ | $CH_2$ |
| $CH(CH_3)_2$ | H | 5-$NO_2$ | H | $CH_2$ |
| $CO_2CH_3$ | H | H | H | $CH_2$ |
| $CO_2CH_3$ | H | H | $OCH_3$ | $CH_2$ |

TABLE Vc

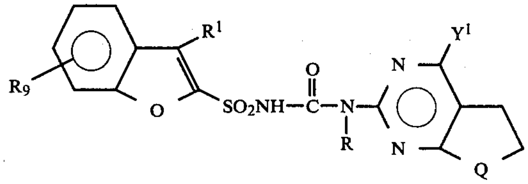

| $R^1$ | R | $R_9$ | $Y^1$ | Q |
|---|---|---|---|---|
| $CO_2CH_3$ | H | H | H | O |
| $SO_2N(CH_3)_2$ | H | H | $CH_3$ | O |
| Cl | H | H | H | O |
| Br | H | 6-$CH_3$ | H | O |
| $NO_2$ | H | H | $CH_3$ | O |
| H | H | H | $CH_3$ | O |
| $CO_2CH_3$ | H | H | $CH_3$ | O |
| $CO_2CH_3$ | H | H | $OCH_3$ | O |
| $CO_2CH_3$ | H | H | Cl | O |
| $CH_3$ | H | 4-Cl | $OCH_3$ | O |
| $CH_2CH_3$ | H | H | $CH_3$ | O |
| $CO_2CH(CH_3)_2$ | H | H | $CH_3$ | O |
| $CO_2CH_3$ | $CH_3$ | H | $CH_3$ | O |
| $CO_2CH_3$ | $CH_3$ | H | $CH_3$ | $CH_2$ |
| $CO_2CH_3$ | H | H | $OCH_3$ | $CH_2$ |
| $CO_2CH(CH_3)_2$ | H | 7-$OCH_3$ | $OCH_3$ | $CH_2$ |
| Cl | H | H | $OCH_3$ | $CH_2$ |
| $NO_2$ | H | H | $OCH_3$ | $CH_2$ |
| H | H | H | $OCH_3$ | $CH_2$ |
| $CH_3$ | H | H | $OCH_3$ | $CH_2$ |
| $C_2H_5$ | H | H | $OCH_3$ | $CH_2$ |
| $CH(CH_3)_2$ | H | 5-$NO_2$ | H | $CH_2$ |
| $CO_2CH_3$ | H | H | H | $CH_2$ |
| $CO_2CH_3$ | H | H | $OCH_3$ | $CH_2$ |

TABLE VI

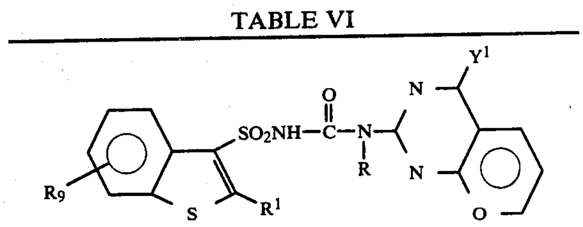

| $R^1$ | R | $R_9$ | $Y^1$ |
|---|---|---|---|
| $CO_2CH_3$ | H | H | H |
| $SO_2N(CH_3)_2$ | H | H | $CH_3$ |
| Cl | H | H | H |
| Br | H | 6-$CH_3$ | H |
| $NO_2$ | H | H | $CH_3$ |
| H | H | H | $CH_3$ |
| $CO_2CH_3$ | H | H | $CH_3$ |
| $CO_2CH_3$ | H | H | $OCH_3$ |
| $CO_2CH_3$ | H | H | Cl |
| $CH_3$ | H | 4-Cl | $OCH_3$ |
| $CH_2CH_3$ | H | H | $CH_3$ |
| $CO_2CH(CH_3)_2$ | H | H | $CH_3$ |
| $CO_2CH_3$ | $CH_3$ | H | $CH_3$ |
| $CO_2CH_3$ | $CH_3$ | 4-$NO_2$ | $CH_3$ |
| $CO_2CH_3$ | H | 4-$OCH_3$ | H |
| $CO_2CH_3$ | H | 7-Br | H |
| $CO_2CH_3$ | H | 5-$NO_2$ | H |

TABLE VIa

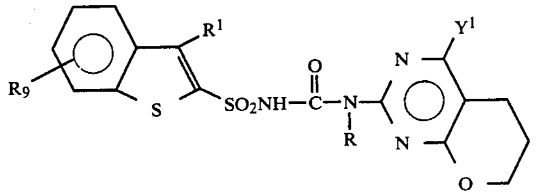

| $R^1$ | R | $R_9$ | $Y^1$ |
|---|---|---|---|
| $CO_2CH_3$ | H | H | H |
| $SO_2N(CH_3)_2$ | H | H | $CH_3$ |
| Cl | H | H | H |
| Br | H | 6-$CH_3$ | H |
| $NO_2$ | H | H | $CH_3$ |
| H | H | H | $CH_3$ |
| $CO_2CH_3$ | H | H | $CH_3$ |
| $CO_2CH_3$ | H | H | $OCH_3$ |
| $CO_2CH_3$ | H | H | Cl |
| $CH_3$ | H | 4-Cl | $OCH_3$ |
| $CH_2CH_3$ | H | H | $CH_3$ |
| $CO_2CH(CH_3)_2$ | H | H | $CH_3$ |
| $CO_2CH_3$ | $CH_3$ | H | $CH_3$ |
| $CO_2CH_3$ | $CH_3$ | 4-$NO_2$ | $CH_3$ |
| $CO_2CH_3$ | H | 4-$OCH_3$ | H |
| $CO_2CH_3$ | H | 7-Br | H |
| $CO_2CH_3$ | H | 5-$NO_2$ | H |

TABLE VIb

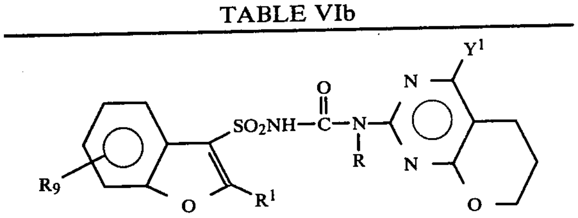

| $R^1$ | R | $R_9$ | $Y^1$ |
|---|---|---|---|
| $CO_2CH_3$ | H | H | H |
| $SO_2N(CH_3)_2$ | H | H | $CH_3$ |
| Cl | H | H | H |
| Br | H | 6-$CH_3$ | H |
| $NO_2$ | H | H | $CH_3$ |

TABLE VIb-continued

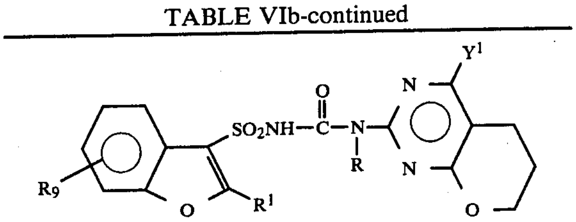

| $R^1$ | R | $R_9$ | $Y^1$ |
|---|---|---|---|
| H | H | H | $CH_3$ |
| $CO_2CH_3$ | H | H | $CH_3$ |
| $CO_2CH_3$ | H | H | $OCH_3$ |
| $CO_2CH_3$ | H | H | Cl |
| $CH_3$ | H | 4-Cl | $OCH_3$ |
| $CH_2CH_3$ | H | H | $CH_3$ |
| $CO_2CH(CH_3)_2$ | H | H | $CH_3$ |
| $CO_2CH_3$ | $CH_3$ | H | $CH_3$ |
| $CO_2CH_3$ | $CH_3$ | 4-$NO_2$ | $CH_3$ |
| $CO_2CH_3$ | H | 4-$OCH_3$ | H |
| $CO_2CH_3$ | H | 7-Br | H |
| $CO_2CH_3$ | H | 5-$NO_2$ | H |

TABLE VIc

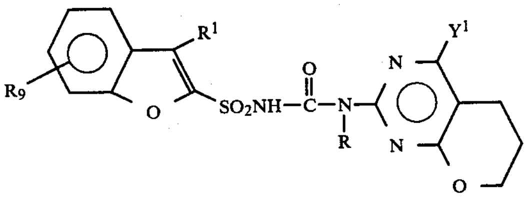

| $R^1$ | R | $R_9$ | $Y^1$ |
|---|---|---|---|
| $CO_2CH_3$ | H | H | H |
| $SO_2N(CH_3)_2$ | H | H | $CH_3$ |
| Cl | H | H | H |
| Br | H | 6-$CH_3$ | H |
| $NO_2$ | H | H | $CH_3$ |
| H | H | H | $CH_3$ |
| $CO_2CH_3$ | H | H | $CH_3$ |
| $CO_2CH_3$ | H | H | $OCH_3$ |
| $CO_2CH_3$ | H | H | Cl |
| $CH_3$ | H | 4-Cl | $OCH_3$ |
| $CH_2CH_3$ | H | H | $CH_3$ |
| $CO_2CH(CH_3)_2$ | H | H | $CH_3$ |
| $CO_2CH_3$ | $CH_3$ | H | $CH_3$ |
| $CO_2CH_3$ | $CH_3$ | 4-$NO_2$ | $CH_3$ |
| $CO_2CH_3$ | H | 4-$OCH_3$ | H |
| $CO_2CH_3$ | H | 7-Br | H |
| $CO_2CH_3$ | H | 5-$NO_2$ | H |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VII

| | Active | Weight Percent* | |
|---|---|---|---|
| | Ingredient | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley & Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 12

Wettable Powder

| | |
|---|---|
| 3-[[(4,6-dimethylpyrimidin-2-yl)aminocarbonyl]aminosulfonyl]benzo[b]thiophene-2-carboxylic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns and then reblended.

EXAMPLE 13

Wettable Powder

| | |
|---|---|
| 3-[[(4,6-dimethoxypyrimidin-2-yl)aminocarbonyl]aminosulfonyl]benzo[b]thiophene-2-carboxylic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled to produce particles essentially all below 10 microns in diameter. The product is reblended before packaging.

EXAMPLE 14

Granule

| | |
|---|---|
| Wettable Powder of Example 13 | 5% |
| attapulgite granules (U.S.S. 20-40 mesh; 0.84-0.42 mm) | 95% |

A slurry of wettable powder containing ≈25% solids is sprayed on the surface of attapulgite granules in a double-cone blender. The granules are dried and packaged.

EXAMPLE 15

Extruded Pellet

| | |
|---|---|
| 3-[[(4-methoxy-6-methylpyrimidin-2-yl)aminocarbonyl]aminosulfonyl]benzo[b]thiophene-2-carboxylic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 16

Oil Suspension

| | |
|---|---|
| 3-[[(4,6-dimethyl-1,3,5-triazin-2-yl)aminocarbonyl]-aminosulfonyl]benzo[b]thiophene-2-carboxylic acid, methyl ester | 25% |
| polyoxyethylene sorbitol hexaoleate | 5% |
| highly aliphatic hydrocarbon oil | 70% |

m

The ingredients are ground together in a sand mill until the solid particles have been reduced to under about 5 microns. The resulting thick suspension may be applied directly, but preferably after being extended with oils or emulsified in water.

EXAMPLE 17

Wettable Powder

| | |
|---|---|
| 3-[[(4,6-dimethoxy-1,3,5-triazin-2-yl)aminocarbonyl]-aminosulfonyl]benzo[b]thiophene-2-carboxylic acid, methyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 m opening) and packaged.

EXAMPLE 18

Low Strength Granule

| | |
|---|---|
| 3-[[(4-methoxy-6-methyl-1,3,5-triazin-2-yl)aminocarbonyl]aminosulfonyl]benzo[b]thiophene-2-carboxylic acid, methyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 19

Aqueous Suspension

| | |
|---|---|
| 3-[[(4,6-dimethylpyrimidin-2-yl)aminocarbonyl]amino-sulfonyl]benzo[b]thiophene-2-carboxylic acid, methyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 20

Solution

| | |
|---|---|
| 3-[[(4,6-dimethoxypyrimidin-2-yl)aminocarbonyl]amino-sulfonyl]benzo[b]thiophene-2-carboxylic acid, methyl ester, sodium salt | 5% |
| water | 95% |

The salt is added directly to the water with stirring to produce the solution, which may then be packaged for use.

EXAMPLE 21

Low Strength Granule

| | |
|---|---|
| 3-[[(4,6-dimethoxypyrimidin-2-yl)aminocarbonyl]amino-sulfonyl]benzo[b]thiophene-2-carboxylic acid, ethyl ester | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 22

Granule

| | |
|---|---|
| 3-[[(4,6-dimethyl-1,3,5-triazin-2-yl)aminocarbonyl]-aminosulfonyl]benzo[b]thiophene-2-carboxylic acid, methyl ester | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 23

High Strength Concentrate

| | |
|---|---|
| 3-[[(4,6-dimethoxy-1,3,5-triazin-2-yl)aminocarbonyl]-aminosulfonyl]benzo[b]thiophene-2-carboxylic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 24

Wettable Powder

| | |
|---|---|
| 3-[[(4-methoxy-6-methyl-1,3,5-triazin-2-yl)aminocarbonyl]aminosulfonyl]benzo[b]thiophene-2-carboxylic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 25

Wettable Powder

| | |
|---|---|
| 3-[[(4-methoxy-6-methyl-1,3,5-triazin-2-yl)aminocarbonyl]aminosulfonyl]benzo[b]thiophene-2-carboxylic acid, methyl ester | 40% |
| sodium ligninsulfonate | 20% |
| montmorillonite clay | 40% |

The ingredients are thoroughly blended, coarsely hammer-milled and then air-milled to produced particles essentially all below 10 microns in size. The material is reblended and then packaged.

EXAMPLE 26

Oil Suspension

| | |
|---|---|
| N—[(4,6-dimethylpyrimidin-2-yl)aminocarbonyl]benzofuransulfonamide, mixture of 2- and 3-positional isomers | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 27

Dust

| | |
|---|---|
| 3-[(4,6-dimethoxypyrimidin-2-yl)aminocarbonyl]aminosulfonyl]benzo[b]thiophene-2-carboxylic acid, methyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

The compounds of the present invention are active herbicides. They have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures. Alternatively, some of the subject compounds are useful for selective pre- or post-emergence weed control in crops, such as wheat and rice. By properly selecting rate and time of application, compounds of this invention may also be used to modify plant growth beneficially.

The precise amount of the compounds of Formula I to be used in any given situation will vary according to the particular end result desired, including their use as selective or general herbicides, the crop species involved, the amount of foilage present, the species of weeds to be controlled, the soil type, the formulation and mode of application, weather conditions, etc. Since so many variables play a role, it is not possible to state a rate of application suitable for all situations. Broadly speaking, the compounds of this invention are used at levels of about 0.02 to 10 kg/ha with a preferred range of 0.04 to 5 kg/ha. In general, the higher rates of application from within this range will be selected for adverse conditions, where extended persistence in soil is desired, or for non-selective weed control purposes.

The compounds of Formula I may be combined with other herbicides and are particularly useful in combination with substituted urea herbicides such as 3-(3,4-dichlorophenyl)-1,1-dimethylurea; the triazines such as 2-chloro-4-(ethylamino)-6-(isopropylamino)-s-triazine; the uracils such as 5-bromo-3-sec-butyl-6-methyluracil; N-(phosponomethyl)glycine; 3-cyclohexyl-1-methyl-6-dimethylamino-s-triazine-2,4(1H,3H)-dione; N,N-dimethyl-2,2-diphenylacetamide; 2,4-dichlorophenoxyacetic acid (and closely related compounds); 4-chloro-2-butynyl-3-chlorophenylcarbamate; diisopropylthiocarbamic acid; ester with 2,3-dichloroallyl alcohol; diisopropylthiocarbamic acid, S-(2,3,3-trichloroallyl ester ethyl-N-benzoyl-N-(3,4-dichlorophenyl)-2-aminopropionate; 1,2-dimethyl-3,5-diphenylpyrazolium methylsulfate; methyl 2-[4-(2,4-dichlorophenoxy)phenoxy]-propanoate; 4-amino-6-tert-butyl-3-(methylthio)-1,2,4-triazin-5(4H)-one; 3-(3,4-dichlorophenyl)-1-methoxy-1-methylurea; 3-isopropyl-1H-2,1,3-benzothiodiazin-(4)-3H-one-2,2-dioxide; α,α,α-trifluoro-2,6-dinitro-N,N-dipropyl-p-toluidine; 1,1′-dimethyl-4,4′-bipyridinium ion; monosodium methanearsonate; 2-chloro-2′,6′-diethyl(methoxymethyl)acetanilide; 1,1-dimethyl-3-(α,α,α-trifluoro-m-tolyl) urea; 2-tert-butyl-4-(2,4-dichloro-5-isopropoxyphenyl-$\Delta^2$-1,3,4-oxadiazolin-5-one; S-(4-chlorobenzyl N,N-diethylthiolcarbomate; N-(butoxymethyl)-2-chloro-2′,6′-diethylacetanilide, 2,4,6-trichlorophenyl-4′-nitrophenyl ether; 2-methylthio-4,6-bis(ethylamino)-S-triazine; 2,4-dichlorophenyl-3′-methoxy-4′-nitrophenyl ether; and S-ethyl hexahydro-1H-azepine-1-carbothioate.

The activity of these compounds was discovered in greenhouse tests. The tests are described and data resulting from them are shown below.

Test Procedure A

Seeds of crabgrass (Digitaria spp.), barnyardgrass (*Echinochloa crusgalli*), wild oats (Avena fatua), cassia (*Cassia tora*), morningglory (Ipomoea spp.), cocklebur (Xanthium spp.), sorghum, corn, soybean, rice, wheat and nutsedge tubers (*Cyperus rotundus*) were planted in a growth medium and treated pre-emergence with the chemicals dissolved in a nonphytotoxic solvent. At the same time, cotton having five leaves (including cotyledonary ones), bush beans with the second trifoliate leaf expanding, crabgrass and barnyardgrass with two leaves, wild oats with one leaf, cassia with three leaves (including cotyledonary ones), morningglory and cocklebur with four leaves (including the cotyledonary ones), sorghum and corn with three leaves, soybean with two cotyledonary leaves, rice with two leaves, wheat with two leaves, and nutsedge with three-five leaves were sprayed. Treated plants and controls were maintained in a greenhouse for sixteen days, then all species were compared to controls and visually rated for response to treatment. The ratings are based on a numerical scale extending from 0=no injury, to 10=complete kill. The accompanying descriptive symbols have the following meanings:

C=chlorosis or necrosis;
D=defoliation;
E=emergence inhibition;
G=growth retardation;
H=formative effects;
S=albinism;
U=unusual pigmentation;
X=axillary stimulation; and
6Y=abscised buds or flowers.

TABLE A
| | kg/ha | BUSH BEAN | POST-EMERGENCE COTTON | MORNINGGLORY | COCKLEBUR | CASSIA | NUTSEDGE | CRABGRASS |
|---|---|---|---|---|---|---|---|---|
| 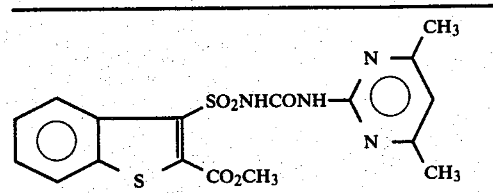 | 0.4 | 9C | 6C, 9G | 4C, 9G | 9C | 2C | 6C, 7G | 3C |
| 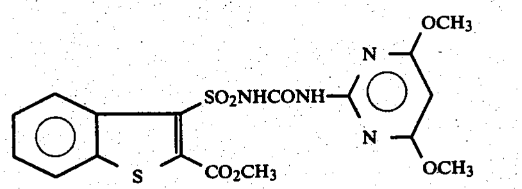 | 0.4 | 9C | 6C, 9G | 9C | 10C | 9C | 4C, 7G | 3C |
| 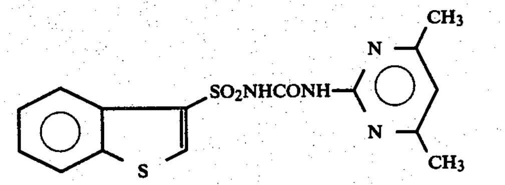 | 2 | 2S, 8G, 6Y | 2C, 2H, 7G | 5C, 9G | 5C, 9G | 2C, 5G | 9C, 9G | 6G |
| | 0.4 | 3S, 7G, 6Y | 3C, 4D, 5G | 3C, 7G | 9C | 4G | 2C, 8G | 0 |
| 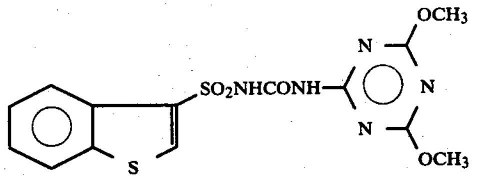 | 2 | 3H, 8G, 6Y | 3C, 3H, 6G | 9C | 9C | 2C, 5G | 5G | 3G |
| | 0.4 | 4S, 7G, 6Y | 2C, 2H, 5G | 10C | 10C | 3C, 5G | 3G | 2G |
| | 2 | 2S, 8G, 6Y | 3C, 2H, 8G | 2C, 5G | 2C, 8G | 4G | 6G | 0 |
| | 0.4 | 2H, 8G, 6X | 2C, 3H, 8G | 2C, 6H | 2C, 7G | 1H | 5G | 0 |
| | Rate kg/ha | | | | | | | |
| Compound 1 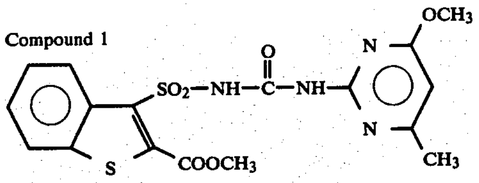 | 0.4 | 6C, 9G | 4C, 7G | 2C, 6G | 10C | 3C | 5G | 2G |

TABLE A-continued
| | POST-EMERGENCE | | | | | | | |
|---|---|---|---|---|---|---|---|---|
| | kg/ha | BARNYARDGRASS | WILD OATS | WHEAT | CORN | SOYBEAN | RICE | SORGHUM |
| Compound 2 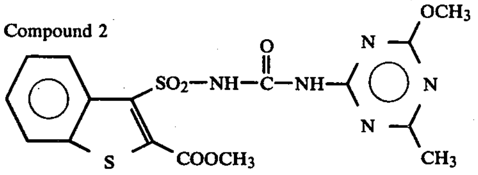 | 0.4 | 7C, 9G | 3C, 5D, 7G | 10C | 10C | 2C, 2H | 3C, 9G | 1C |
| Compound 3 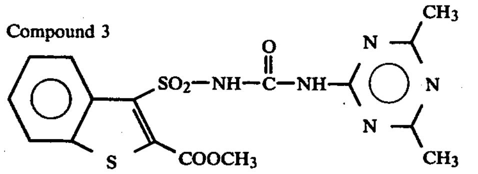 | 0.05 | 1C, 9G, 6Y | 1C | 1C, 5G | 9C | 1C, 5G | 5G | 0 |
| Compound 4 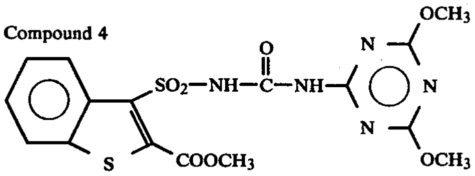 | 0.4 | 9D, 9G, 6Y | 3C, 5G | 9C | 10C | 1C, 5G | 2C, 9G | 4G |
| Compound 5 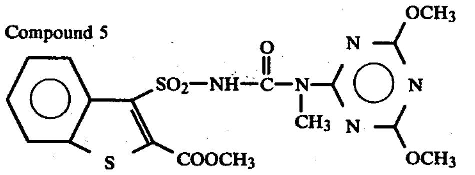 | 0.4 | 2C, 3H | 3C, 5G | 2C, 5G | 3C, 9G | 2C, 5G | 0 | 2C |
| Compound 6 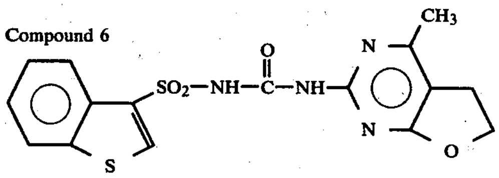 | 0.4 | 9C | 2C, 1H | 3C, 8G | 9C | 2C, 5G | 5C, 9G | 2C, 5H |

TABLE A-continued
| | | | | | | | | | |
|---|---|---|---|---|---|---|---|---|---|
| 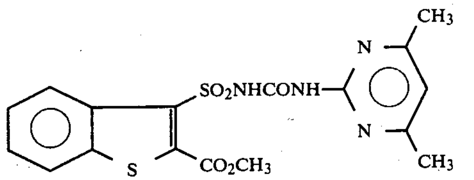 | 0.4 | 5C, 9H | 2C, 6G | 1C, 5G | 5G | 5C, 9G | 2C, 6G | 2C, 9H |
| 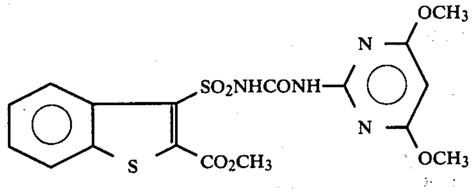 | 0.4 | 4C, 9H | 0 | 2G | 4C, 9G | 6C, 9G | 4C, 7G | 2C, 8G |
| 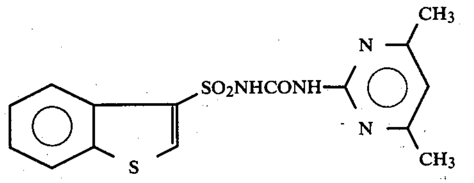 | 2 | 2C, 7G | 3G | 2G | 9H | 4H, 8G | 6G | 7G |
| | 0.4 | 1C, 5G | 2G | 3G | 8H | 5C, 9G | 5G | 1C, 8H |
| 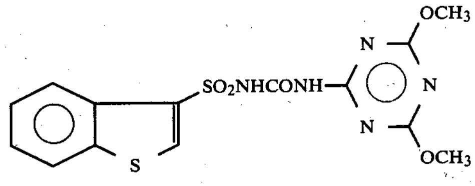 | 2 | 2C, 7G | 0 | 2G | 8H | 5C, 9G | 4C, 8G | 9G |
| | 0.4 | 3G | 0 | 0 | 6H | 5C, 9G | 4C, 8G | 8G |
| | 2 | 1C | 0 | 0 | 6G | 5C, 9G | 3C, 5G | 5G |
| | 0.4 | 0 | 0 | 0 | 2G | 5C, 9G | 5G | 5G |
| | Rate kg/ha | | | | | | | |
| Compound 1 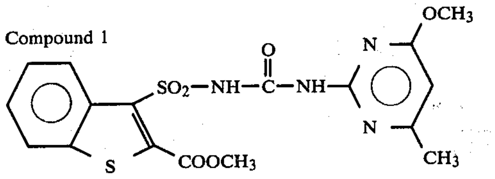 | 0.4 | 2C, 5H | 0 | 0 | 2C, 6G | 9C | 2C, 6G | 2C, 9H |

TABLE A-continued
| | kg/ha | MORNING-GLORY | COCKLE-BUR | CASSIA | NUT-SEDGE | CRAB-GRASS | BARNYARD-GRASS | WILD OATS | WHEAT | CORN | SOY-BEAN | RICE | SORGHUM |
|---|---|---|---|---|---|---|---|---|---|---|---|---|---|
| Compound 2 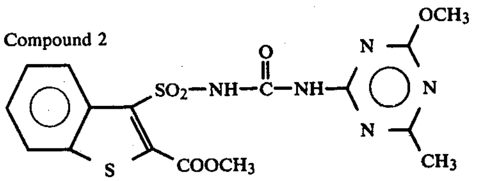 | 0.4 | 2C, 5H | 2C, 3G | 3G | 2C, 3G | 9C | — | 2C, 9H | | | | | |
| Compound 3 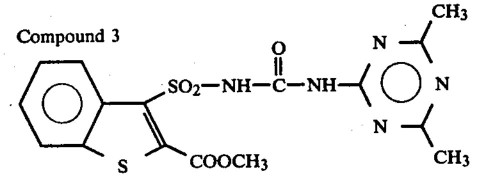 | 0.05 | 0 | 0 | 0 | 0 | 2C, 7H | 1C, 4G | 1C, 5G | | | | | |
| Compound 4 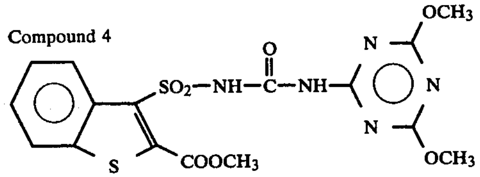 | 0.4 | 2C, 6H | 6G | 2C | 2C, 5G | 6C, 9G | 3C, 8G | 2C, 8H | | | | | |
| Compound 5 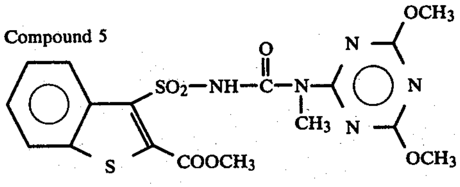 | 0.4 | 2C, 6G | 0 | 0 | 1C, 2G | 3C, 9G | 4G | 1C, 6G | | | | | |
| Compound 6 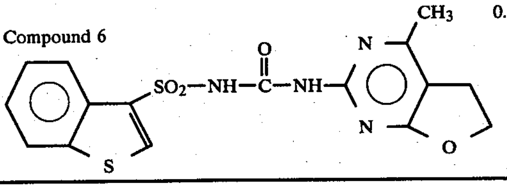 | 0.4 | 2C, 6H | 2C, 7G | 1C | 1C, 4G | 2C, 9G | 2C, 9G | 2C, 9H | | | | | |
PRE-EMERGENCE TABLE A-continued
| | Rate kg/ha | | | | | | | | | | | | |
|---|---|---|---|---|---|---|---|---|---|---|---|---|---|
| 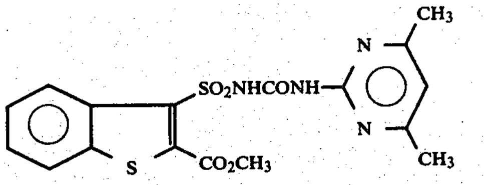 | 0.4 | 9G | 9G | 8G | 10E | 1C, 5G | 2C, 9H | 1C, 8G | 5G | 1C, 7G | 9H | 10E | 2C, 9H |
| 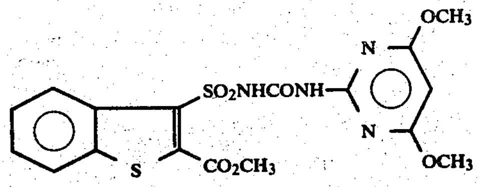 | 0.4 | 9G | 9H | 9G | 10E | 4G | 9H | 5G | 4G | 1C, 9H | 8H | 10E | 9H |
| 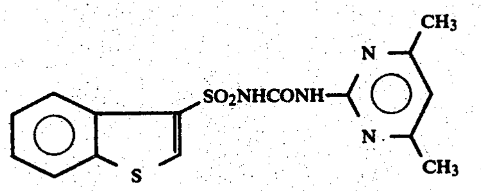 | 2 | 9H | 9G | 9G | 10E | 3C, 7G | 2C, 9H | 8G | 9G | 3C, 9H | 9H | 9H | 9H |
| | 0.4 | 9G | 8G | 8G | 10E | 3C, 5G | 3S, 9G | 8G | 7G | 9H | 8H | 9H | 9H |
| | 2 | 9G | 9G | 9G | 8G | 2C | 3C | 6G | 4G | 9G | 9H | 10E | 9H |
| | 0.4 | 9G | 8G | 8G | 2C, 8G | 3G | 3S, 8G | 2G | 3G | 9G | 9H | 10E | 9G |
| 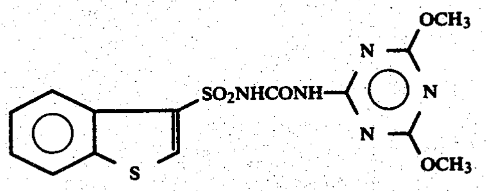 | 2 | 9G | 9G | 9G | 10E | 2C, 6G | 3C, 8G | 6G | 4G | 9G | 9H | 10E | 2C, 9G |
| | 0.4 | 9G | 9C | 9G | 2C, 9G | 4G | 4S, 7G | 0 | 0 | 7G | 3H, 8G | 9H | 6G |
| Compound 1 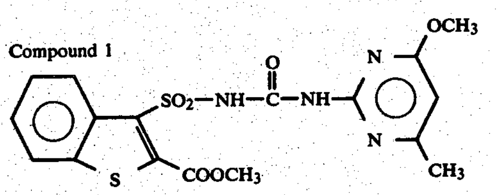 | 0.4 | 8G | 8H | 8G | 10E | 1C, 3G | 2C, 7H | 5G | 6G | 2U, 9H | 9H | 10E | 3C, 9H |

TABLE A-continued
| | | | | | | | | | | | | | |
|---|---|---|---|---|---|---|---|---|---|---|---|---|---|
| Compound 2 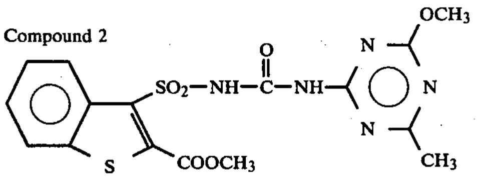 | 0.4 | 9G | 9H | 9G | 10E | 2G | 2C, 5G | 1C, 5G | 3G | 1C, 7G | 9H | 10E | 1C, 7H |
| Compound 3 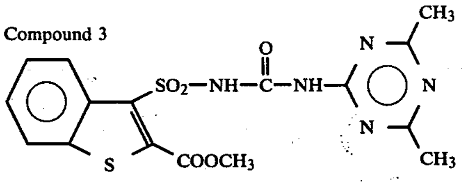 | 0.05 | 1C, 5G | 9H | 1C, 5G | 8G | 1C | 0 | 0 | 0 | 1G | 1C | 2C, 3G | 1C, 3G |
| Compound 4 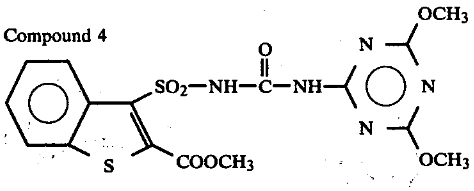 | 0.4 | 9H | 9H | 8G | 10E | 1C | 2C | 1C, 8G | 1C, 3G | 2C, 7G | 9H | 10E | 2C, 7G |
| Compound 5 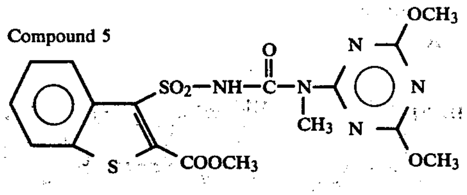 | 0.4 | 0 | 0 | 0 | 0 | 0 | 0 | 0 | 0 | 0 | 1H | 3G | 0 |
| Compound 6 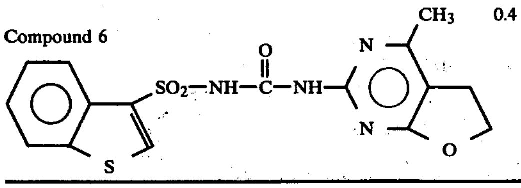 | 0.4 | 9H | — | 8H | 10E | 5G | 2C, 8H | 2C, 9G | 1C, 6G | 2C, 7H | 9H | 9H | 5C, 9H |

Test Procedure B

The following table, Table B, is presented to additionally illustrate the biological activity of the compounds of the present invention. The data illustrate the efficacy of the compounds for the control of weeds in rice cultures.

Tests were conducted in which rice plants were transplanted into paddies containing soil, sprouting barnyardgrass (*Echinochloa crusgalli*) seeds, sprouting water chestnut tubers, seeds of *Scirpus mucronatus* and arrowhead (*Saggittaria latifolia*) tubers (sprouting in one of the tests). The test compounds were applied directly into the water (the water level was maintained at a few cm above the soil surface) three to four days after transplanting of rice. Early ratings (same system as described in earlier tables) were taken on rice one week after application of the test compounds; late ratings were taken on all species about three weeks after application.

TABLE B

| COMPOUND | RATE, Kg/HA | RICE (EARLY RATING) | RICE (LATE RATING) | BARNYARD GRASS | WATER CHESTNUT | *Scirpus mucronatus* | Arrowhead* |
|---|---|---|---|---|---|---|---|
| 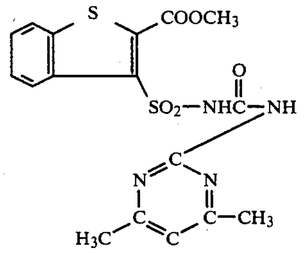 | 25 | 0 | 0 | 0 | 7G | 9C | — |
| | 100 | 0 | 5G | 5G | 9G1C | 9C | — |
| 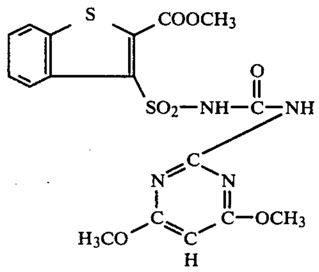 | 25 | 0 | 0 | 9C | 10G2C | 10C | — |
| | 100 | 0 | 2G | 7G6C | 8G1C | 10C | — |
| 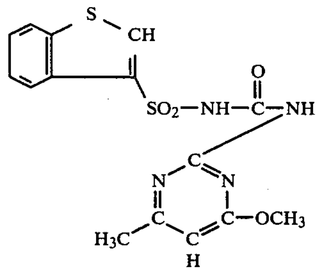 | 75 | 0 | 0 | 0 | 0 | 0 | 8G |
| | 300 | 4C | 1C | 3G | 2G | 9C | 10G |

*A dash (—) indicates that no rating was made because of variable establishment of the plant in the particular test.

Test Procedure C

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test Procedure A. The data are summarized in Table C. The data show that certain compounds from the scope of the invention are useful for the pre-emergence control of weeds in wheat.

TABLE C

Pre-Emergence on Fallsington Silt Loam

Compound 1

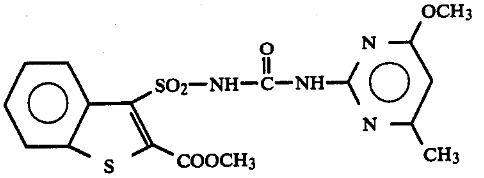

Compound 2

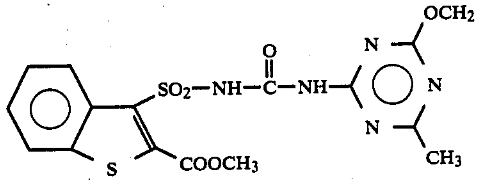

| | Compound 1 | | Compound 2 | |
|---|---|---|---|---|
| Rate kg/ha | .06 | 0.25 | 0.06 | 0.25 |
| Crabgrass | 0 | 0 | 0 | 0 |
| Barnyardgrass | 0 | 3G | 0 | 0 |
| Sorghum | 3G | 5G, 3H | 3G | 6G, 3H |
| Wild Oats | 0 | 3G | 3G | 6G |
| Johnsongrass | 0 | 2G | 0 | 0 |
| Dallisgrass | 0 | 0 | 0 | 0 |
| Giant foxtail | 0 | 3G | 0 | 0 |
| Ky. bluegrass | 5G | 6G, 3C | 0 | 4G |
| Cheatgrass | 4G | 4G | 5G | 5G |
| Sugarbeets | 4G | 7G, 8C | 8G, 8C | 10C |
| Corn | 0 | 2G | 0 | 0 |
| Mustard | 5G | 10C | 10C | 10C |
| Cocklebur | 0 | 5G, 5H | 7G, 5H | 8G, 8C |
| Pigweed | — | — | — | — |
| Nutsedge | 0 | 0 | 8G | 5G |
| Cotton | 0 | 0 | 0 | 4G |
| Morningglory | 0 | 0 | 6G | 7G |
| Cassia | — | 0 | 6G | 8G, 8C |
| Teaweed | 3G | 7G, 5C | 7G, 2C | 7G, 3C |
| Velvetleaf | 0 | 6G, 5H | 5G, 3H | 8G, 5H |
| Jimsonweed | 0 | 4G | 7G, 4C | 8G, 6C |
| Soybean | 0 | 5G, 2C | 6G, 5H | 7G, 5H |
| Rice | 4G | 6G, 2C | 6G, 3C | 8G, 8E |
| Wheat | 0 | 0 | 0 | 0 |

Test Procedure D

Twenty-five cm diameter plastic pots filled with Fallsington silt loam were planted with soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pensylvanicum*), crabgrass (Digitaria spp.), nutsedge (*Cyperus rotundus*), barnyardgrass (*Echinochloa crus-galli*), giant foxtail (*Setaria faberii*) and wild oats (*Avena fatua*). Approximately 2½ weeks after planting, the young plants and the soil around them were sprayed overall with the test chemical dissolved in a non-phytotoxic solvent. Fourteen days after treatment, all species were compared to untreated controls and visually rated for response to treatment. The rating system was as described previously for Test Procedure A. The data are presented in Table D. The compound tested by this procedure is useful for the post-emergence control of weeds in wheat.

TABLE D

Over-the-Top Soil/Foliage Treatment

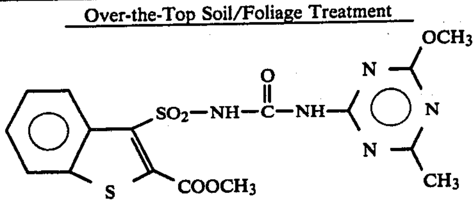

| Rate kg/ha | 0.12 | 0.5 |
|---|---|---|
| Soybeans | 10G, 7C | 10G, 7C |
| Velvetleaf | 10G, 8C | 10C |
| Sesbania | 10G, 6C | 10G, 7C |
| Cassia | 7G, 3C | 9G, 4C |
| Cotton | 8G, 5C | 8C, 10G |
| Morningglory | 9G, 6C | 9G, 7C |
| Alfalfa | 10C | 10C |
| Jimsonweed | 9G, 3C | 10G, 7C |
| Cocklebur | 10G, 7C | 10G, 9C |
| Corn | — | 1G, 1C |
| Crabgrass | 4G | 5G |
| Rice | 3G | 5G |
| Nutsedge | 4G | 10G, 4C |
| Barnyardgrass | 2G | 3G |
| Wheat | 0 | 0 |
| Giant foxtail | 0 | 3G |
| Wild Oats | 2G, 1C | 4G, 1C |
| Sorghum | 7G, 1C | 9G, 3C |

What is claimed is:

1. A compound of the formula:

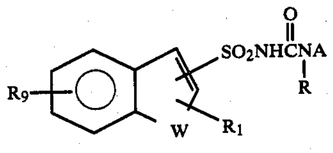

I wherein

R is H or $CH_3$;

$R^1$ is H, Cl, Br, $NO_2$, $C_1$-$C_3$ alkyl, $C_1$-$C_3$ alkoxy, $CO_2R^2$, $C(O)NR^3R^4$, $SO_2R^5$ or $SO_2NR^6R^7$;

$R^2$ is $C_1$-$C_4$ alkyl, $C_3$-$C_4$ alkenyl, $CH_2CH_2OCH_3$, $CH_2CH_2OC_2H_5$, $CH_2CH_2CH_2OCH_3$ or $CH_2R^8$;

$R^3$ is $C_1$-$C_4$ alkyl;

$R^4$ is H, $C_1$-$C_4$ alkyl or $OCH_3$; or $R^3$ and $R^4$ can be taken together to form $-(CH_2)_4-$;

$R^5$ is $C_1$-$C_4$ alkyl;

$R^6$ is $C_1$-$C_3$ alkyl or $OCH_3$;

$R^7$ is $C_1$-$C_3$ alkyl;

$R^8$ is $C_1$-$C_3$ alkyl substituted with 1-3 atoms of F, Cl, or Br;

$R^9$ is H, $CH_3$, $OCH_3$, Cl, Br or $NO_2$; W is O or S;

A is

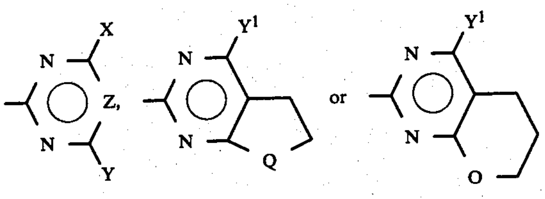

X is H, $CH_3$, $OCH_3$, $OC_2H_5$, $OCH_2CF_3$, $CH_2OCH_3$ or Cl;

Y is $CH_3$, $OCH_3$, $OC_2H_5$, $NH_2$, $NHCH_3$, $N(CH_3)_2$ or $SCH_3$;

Z is N, CH, C—Cl, C—Br, C—CN, C—$CH_3$, C—$C_2H_5$, C—$CH_2CH_2Cl$ or C—$CH_2CH=CH_2$;

$Y^1$ is H, $CH_3$, $OCH_3$ or Cl; and

Q is O or $CH_2$;

provided that (1) when $R^4$ or $R^6$ is $OCH_3$, then $R^3$ or $R^7$ is $CH_3$;

(2) the total number of carbon atoms of either $R^3$ and $R^4$, or $R^6$ and $R^7$, is less than or equal to 4; and (3) when X is Cl, then Z is CH.

2. A compound of claim 1 wherein Z is N or CH; and $R^1$ is H, Cl, Br, $NO_2$, $C_1$-$C_3$ alkyl, $CO_2R^2$, $SO_2R^5$ or $SO_2NR^6R^7$.

3. A compound of claim 2 wherein $R^9$ is H.

4. A compound of claim 3 wherein R is H.

5. A compound of claim 4 wherein

A is

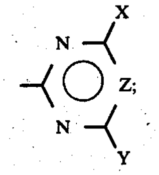

X is $CH_3$, $OCH_3$, $OC_2H_5$ or $CH_2OCH_3$; and

Y is $CH_3$ or $OCH_3$.

6. A compound of claim 5 wherein W is S.

7. A compound of claim 6 wherein $R^1$ is Cl, Br, $NO_2$, $CO_2R^2$, $SO_2R^5$ or $SO_2NR^6R^7$.

8. A compound of claim 7 wherein $R^1$ is at the 2-position of the benzo[b]thiophene ring.

9. A compound of claim 8 wherein $R^1$ is $CO_2R^2$.

10. The compound of claim 1, 3-[[(4,6-dimethylpyrimidin-2-yl)aminocarbonyl]aminosulfonyl]benzo[b]-thiophene-2-carboxylic acid, methyl ester.

11. The compound of claim 1, 3-[[(4,6-dimethoxypyrimidin-2-yl)aminocarbonyl]aminosulfonyl]benzo[b]thiophene-2-carboxylic acid, methyl ester.

12. The compound of claim 1, 3-[[(4-methoxy-6-methylpyrimidin-2-yl)aminocarbonyl]aminosulfonyl]-benzo[b]thiophene-2-carboxylic acid, methyl ester.

13. The compound of claim 1, 3-[[(4,6-dimethyl-1,3,5-triazin-2-yl)aminocarbonyl]aminosulfonyl]benzo[b]thiophene-2-carboxylic acid, methyl ester.

14. The compound of claim 1, 3-[[(4,6-dimethoxy-1,3,5-triazin-2-yl)aminocarbonyl]aminosulfonyl]benzo[b]thiophene-2-carboxylic acid, methyl ester.

15. The compound of claim 1, 3-[[(4-methyl-6-methoxy-1,3,5-triazin-2-yl)aminocarbonyl]aminosulfonyl]benzo[b]thiophene-2-carboxylic acid, methyl ester.

16. The compound of claim 1, 3-[[(4,6-dimethoxypyrimidin-2-yl)aminocarbonyl]aminosulfonyl]benzo[b]-thiophene-2-carboxylic acid, ethyl ester.

17. A compound selected from:

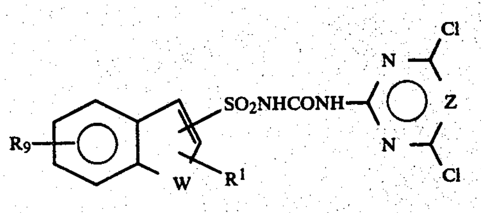

$R^1$ is H, Cl, Br, $NO_2$, $C_1$-$C_3$ alkyl, $C_1$-$C_3$ alkoxy, $CO_2R^2$, $C(O)NR^3R^4$, $SO_2R^5$ or $SO_2NR^6R^7$;

$R^2$ is $C_1$-$C_4$ alkyl, $C_3$-$C_4$ alkenyl, $CH_2CH_2OCH_3$, $CH_2CH_2OC_2H_5$, $CH_2CH_2CH_2OCH_3$ or $CH_2R^8$;

$R^3$ is $C_1$-$C_4$ alkyl;

$R^4$ is H, $C_1$-$C_4$ alkyl or $OCH_3$; or $R^3$ and $R^4$ can be taken together to form —$(CH_2)_4$—;

$R^5$ is $C_1$-$C_4$ alkyl;

$R^6$ is $C_1$-$C_3$ alkyl or $OCH_3$;

$R^7$ is $C_1$-$C_3$ alkyl;

$R^8$ is $C_1$-$C_3$ alkyl substituted with, 1-3 atoms of F, Cl, or Br;

$R^9$ is H, $CH_3$, $OCH_3$, Cl, Br or $NO_2$;

W is O or S; and

Z is N or CH.

18. A compound selected from:

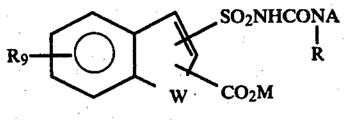

wherein

M is H or alkali metal ion;

R is H or $CH_3$;

$R^9$ is H, $CH_3$, $OCH_3$, Cl, Br or $NO_2$;

W is O or S;

A is

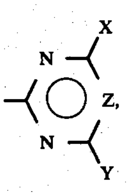

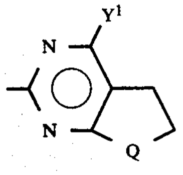

or

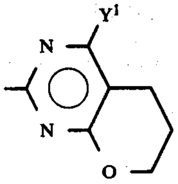

X is H, $CH_3$, $OCH_3$, $OC_2H_5$, $OCH_2CF_3$, $CH_2OCH_3$;

Y is $CH_3$, $OCH_3$, $OC_2H_5$, $NH_2$, $NHCH_3$, $N(CH_3)_2$ or $SCH_3$;

Z is N, CH, C—Cl, C—Br, C—CN, C—$CH_3$, C—$C_2H_5$, C—$CH_2CH_2Cl$ or C—$CH_2CH=CH_2$;

$Y^1$ is H, $CH_3$, $OCH_3$; and

Q is O or $CH_2$.

19. A composition for controlling the growth of undesired vegetation which comprises an effective amount of a compound of claim 1 and at least one of the following: surfactant, solid or liquid diluent.

20. A composition for controlling the growth of undesired vegetation which comprises an effective amount of a compound of claim 2 and at least one of the following: surfactant, solid or liquid diluent.

21. A composition for controlling the growth of undesired vegetation which comprises an effective amount of a compound of claim 3 and at least one of the following: surfactant, solid or liquid diluent.

22. A composition for controlling the growth of undesired vegetation which comprises an effective amount of a compound of claim 4 and at least one of the following: surfactant, solid or liquid diluent.

23. A composition for controlling the growth of undesired vegetation which comprises an effective amount of a compound of claim 5 and at least one of the following: surfactant, solid or liquid diluent.

24. A composition for controlling the growth of undesired vegetation which comprises an effective amount of a compound of claim 6 and at least one of the following: surfactant, solid or liquid diluent.

25. A composition for controlling the growth of undesired vegetation which comprises an effective amount of a compound of claim 7 and at least one of the following: surfactant, solid or liquid diluent.

26. A composition for controlling the growth of undesired vegetation which comprises an effective amount of the compound of claim 8 and at least one of the following: surfactant, solid or liquid diluent.

27. A method for controlling the growth of undesired vegetation which comprises applying to the locus to be protected an effective amount of a compound of claim 1.

28. A method for controlling the growth of undesired vegetation which comprises applying to the locus to be protected an effective amount of a compound of claim 2.

29. A method for controlling the growth of undesired vegetation which comprises applying to the locus to be protected an effective amount of a compound of claim 3.

30. A method for controlling the growth of undesired vegetation which comprises applying to the locus to be protected an effective amount of a compound of claim 4.

31. A method for controlling the growth of undesired vegetation which comprises applying to the locus to be protected an effective amount of a compound of claim 5.

32. A method for controlling the growth of undesired vegetation which comprises applying to the locus to be protected an effective amount of a compound of claim 6.

33. A method for controlling the growth of undesired vegetation which comprises applying to the locus to be protected an effective amount of a compound of claim 7.

34. A method for controlling the growth of undesired vegetation which comprises applying to the locus to be protected an effective amount of the compound of claim 8.

35. A method for controlling the growth of undesired vegetation in rice which comprises applying to the locus of the rice an effective amount of the compound of claim 11.

* * * * *